(12) United States Patent
Possiel et al.

(10) Patent No.: US 11,377,463 B2
(45) Date of Patent: Jul. 5, 2022

(54) CLASS OF SUCROSE ESTERS AND A METHOD FOR THEIR PREPARATION

(71) Applicant: Julius-Maximilians-Universitaet Wuerzburg, Wuerzburg (DE)

(72) Inventors: Christian Possiel, Gerbrunn (DE); Juergen Seibel, Wuerzburg (DE)

(73) Assignee: Julius-Maximilians-Universitaet Wuerzburg, Wuerzburg (DE)

( * ) Notice: Subject to any disclaimer, the term of this patent is extended or adjusted under 35 U.S.C. 154(b) by 48 days.

(21) Appl. No.: 16/645,380

(22) PCT Filed: Aug. 29, 2018

(86) PCT No.: PCT/EP2018/073258
§ 371 (c)(1),
(2) Date: Mar. 6, 2020

(87) PCT Pub. No.: WO2019/043069
PCT Pub. Date: Mar. 7, 2019

(65) Prior Publication Data
US 2021/0047356 A1     Feb. 18, 2021

(30) Foreign Application Priority Data

Aug. 29, 2017 (EP) ..................... 17001445

(51) Int. Cl.
*C07H 7/033*    (2006.01)
*C12P 19/12*    (2006.01)
*C12P 19/18*    (2006.01)

(52) U.S. Cl.
CPC .............. *C07H 7/033* (2013.01); *C12P 19/12* (2013.01); *C12P 19/18* (2013.01)

(58) Field of Classification Search
CPC . C07H 1/00; C07H 7/033; C12P 19/12; C12P 19/18
See application file for complete search history.

(56) References Cited

FOREIGN PATENT DOCUMENTS

| DE | 195 42 303 A1 | 5/1997 |
| DE | 197 16 731 A1 | 10/1998 |
| EP | 0 599 646 A2 | 6/1994 |
| EP | 0 651 734 A1 | 5/1995 |

OTHER PUBLICATIONS

Deng et al., Selective chemical depolymerization of rhamnogalacturonans. Carbohydrate Res., 2006, vol. 341: 474-484. (Year: 2006).*

Hestrin et al., The Mechanism of Polysaccharide Production from Sucrose 5. Transfer of Fructose To C-1 of Aldose By LEV Ansucrase*. Biochemical Journal, 1958, vol. 69(3): 388-398. (Year: 1958).*

Homann et al., Insights into polymer versus oligosaccharide synthesis: mutagenesis and mechanistic studies of a novel levansucrase from Bacillus megaterium. Biochem. J., 2007, vol. 407: 189-198. (Year: 2007).*

Strube et al., Polysaccharide Synthesis of the Levansucrase SacB from Bacillus megaterium Is Controlled by Distinct Surface Motifs. The J. Biol. Chem., 2011, vol. 286(20): 17593-17600. (Year: 2011).*

Yuan et al., Identification of Key Constituents and Structure of the Extracellular Polymeric Substances Excreted by Bacillus megaterium TF10 for Environ. Sci., Technol., 2011, vol. 15: 1152-1157. (Year: 2011).*

* cited by examiner

*Primary Examiner* — Ganapathirama Raghu
(74) *Attorney, Agent, or Firm* — Smith Patent, LLC; Chalin A. Smith

(57) ABSTRACT

A new class of sucrose esters and a method for their preparation is described herein.

7 Claims, 25 Drawing Sheets

CLASS OF SUCROSE ESTERS AND A METHOD FOR THEIR PREPARATION

This application corresponds to the U.S. National Phase of International Application No. PCT/EP2018/073258 filed Aug. 29, 2018, which, in turn, claims priority to European Patent Application No. 17.001445.0 filed Aug. 29, 2017, the contents of which are incorporated by reference herein in their entirety.

TECHNICAL FIELD

The present invention relates to a new class of sucrose esters and a method for their preparation.

BACKGROUND

Carbohydrates are an important source of renewable compounds. The disaccharide sucrose (a-D-glucopyranosyl-(1,2)-β-D-fructofuranoside) is produced in industrial scale of $170 \times 10^6$ MT/y. The development of chemical processes from carbohydrates instead of fossil resources became a principal of Green Chemistry. Sucrose esters are one of this examples. They have many applications in food, cosmetics and pharmaceutical industry. Sucrose possesses 8 hydroxyl groups that can be esterified for example with fatty acids with aliphatic tails of 1 to 18 carbons (L. Osipow, F. D. Snell, W. C. York and A. Finchler, *Industr Eng Chem,* 1956, 48, 1459-1462). The chemical production of sucrose esters has been investigated (L. I. Osipow and W. Rosenblatt, *J Am Oil Chem Soc,* 1967, 44, 307-309) but the selectivity in the synthesis of these esters remains a challenge. Lipases from i.e. *Thermomyces lanuginosus, Candida antarctica* and *Rhizomucor miehei* catalyze the transesterification to 2-O-acylsucrose or 6-O-acylsucrose. Most are mixtures of double esterification. All these sucrose esters derive from a carboxylic acid (fatty acid) and sucrose equipped with hydroxyl-groups.

However, known methods yield mixtures of sucrose esters with different acylation pattern.

SUMMARY

In view of the above drawbacks of the prior art it would be desirable to provide a method which allows the selective mono esterification of position 6 in sucrose.

The inventors now found that under certain conditions D-uronic acid can be fructosylated by the levansucrase from *B. megaterium.* It was found that in the presence of D-glucuronic acid this enzyme is deactivated. However, it was also found that the desired fructosylation reaction occurs if either a salt of the D-uronic acid or an ester of the D-uronic acid is employed.

Therefore, the present invention relates to a method for the preparation of a β-D-fructofuranosyl-(2,1)-α-D-uronic acid or an ester thereof which comprises the step of fructosylation of a D-uronic acid salt or ester thereof in the presence of *B. megaterium* levansucrase (Bm-Ls).

The inventors furthermore found that the esterification of D-uronic acid using an organic halide can be conducted with high yield of the desired D-uronic acid ester in the presence of tetrabutylammonium fluoride (TBAF).

The present invention therefore also relates to a method for the preparation of a D-uronic acid ester comprising the step of reacting D-uronic acid with an organic halide in the presence of tetrabutylammonium fluoride.

The invention furthermore relates to

β-D-fructofuranosyl-(2,1)-α-D-uronic acid mono ester as a new class of sucrose esters;

β-D-fructofuranosyl-(2,1)-α-D-galacturonic acid as a precursor for ester synthesis;

β-D-fructofuranosyl-(2,1)-α-D-6-p-toluensulfonylglycopyranoside as a precursor for ester synthesis;

β-D-fructofuranosyl-(2,1)-α-D-6-azidoglycopyranoside as a precursor for ester synthesis and general conjugation;

β-p-D-fructofuranosyl-(2,1)-α-D-6-p-toluensulfonylglycopyranoside as a precursor for ester synthesis and general conjugation.

DETAILED DESCRIPTION

SacB belongs to the family of glycoside hydrolases 68 (GH 68) (V. Lombard, H. G. Ramulu, E. Drula, P. M. Coutinho and B. Henrissat, *Nucleic Acids Res,* 2014, 42, D490-D495) and mainly catalyzes hydrolysis of sucrose although it also transfers fructosyl units to sucrose resulting in β(2→6)-linked fructans (M. Elena Ortiz-Soto, C. Possiel, J. Gorl, A. Vogel, R. Schmiedel and J. Seibel, *Glycobiol,* 2017, 27, 755-765; A. Homann, R. Biedendieck, S. Gotze, D. Jahn and J. Seibel, *Biochem J,* 2007, 407, 189-198). In previous work α(1→2)-linked sucrose analogues were synthesized enzymatically with levansucrase from Bacillus megaterium (SacB) in the presence of glycopyranose acceptors like D-galactose or D-xylose up to 60% yield (C. P. Strube, A. Homann, M. Gamer, D. Jahn, J. Seibel and D. W. Heinz, *J Biol Chem,* 2011, 286, 17593-17600; M. E. Ortiz-Soto, M. Rivera, E. Rudino-Pinera, C. Olvera and A. Lopez-Munguia, *PEDS,* 2008, 21, 589-595).

The catalytic triad of the *B. megaterium* levansucrase (Bm-Ls) consists the nucleophile D95, the transition state stabilizer D257 and the acid/base catalyst E352 (Scheme 1). The substitution of the glucopyranoside is initiated by protonation of the glycosidic bond of sucrose with E352, followed by a nucleophilic attack of D95 to form a covalent fructosyl-enzyme intermediate (Scheme 1c) by inverting the stereogenic center of C-2 (α-configuration). The mechanism undergoes an oxocarbenium ion-like transition state (TS1, Scheme 1). Then the acceptor substrate attacks in a $S_N i/S_N 2$ mechanism to finally yield the fructosylated acceptor substrate.

Scheme 1

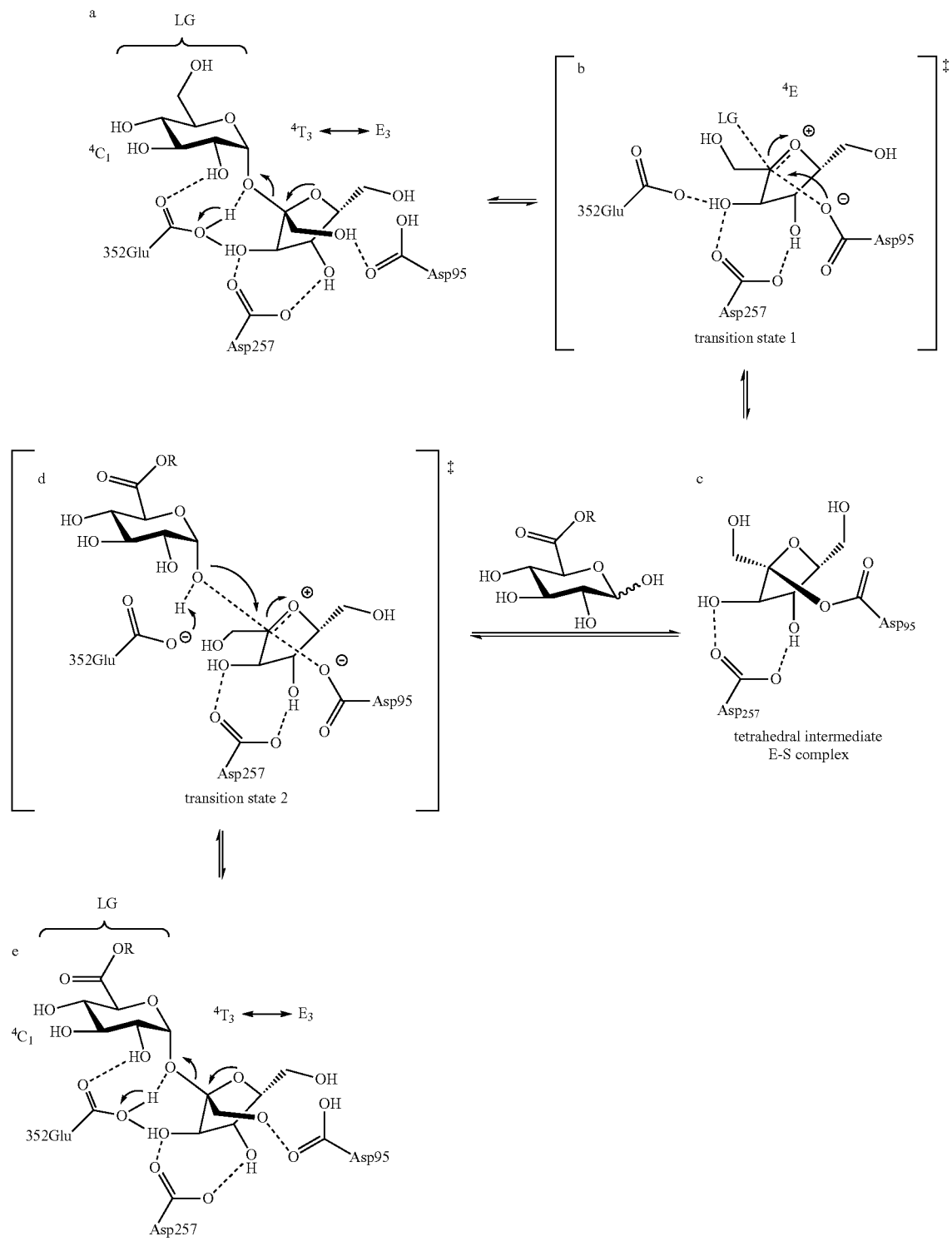

Unanticipated the inventors observed the deactivation of the enzyme by using D-glucuronic acid (500 mM) as acceptor substrate. It was found that the deactivation can be avoided if the sodium salt of the glucuronic acid (500 mM) was used in the enzymatic reaction as acceptor and indeed the desired sucrose analogue 8-D-fructofuranosyl-(2,1)-α-D-glucuronic acid 2a (see Scheme 2) has been formed up to 43% (78 g/l, FIG. 1). Because galactose has proven to be a good acceptor, it was anticipated that D-galacturonic acid 6a would lead to the similar fructosylation. 8-D-fructofuranosyl-(2,1)-α-D-galacturonic acid 3a was formed in 40% (700, FIG. 1) yield.

The present invention therefore relates to a method for the preparation of a 8-D-fructofuranosyl-(2,1)-α-D-uronic acid or an ester thereof which comprises the step of fructosylation of a D-uronic acid salt or ester thereof in the presence of B. megaterium levansucrase (Bm-Ls).

In the context of the present invention, any D-uronic acid ester is to be understood as the mono ester, which is derived from the acid group of the uronic acid.

In one embodiment, the D-uronic acid is D-glucuronic acid or D-galacturonic acid.

In one embodiment, the D-uronic acid salt is an alkali metal salt, such as a sodium or potassium salt, preferably a sodium salt.

The ester can be derived from a D-uronic acid residue and any alcohol residue. Suitable esters are known to a person skilled in the art. For example, the ester can be a residue of the formula —CO—O—R, wherein R is a hydrocarbon residue having 1 to 30 carbon atoms which may be interrupted by one or more heteroatoms (such as oxygen, nitrogen, sulfur, and phosphor) and which may be substituted by one or more functional groups (such as halogen, alcohol, ketone, aldehyde, carboxylic acid, ester, amide, amine, imide, azide, azo, cyanate, nitrate, thiol, sulfonic acid, thiocyanate, and phosphate).

If in the method of the invention it is desired to obtain a 8-D-fructofuranosyl-(2,1)-α-D-uronic acid ester, it is possible that the esterification is conducted either prior or after the fructosylation step.

In one embodiment, the esterification is conducted using for example an organic halide as explained below in the presence of tetrabutylammonium fluoride (TBAF). It was found that using TBAF increases the yield of the desired ester.

In another embodiment, the invention relates to a method for the preparation of a D-uronic acid ester comprising the step of reacting D-uronic acid with an organic halide in the presence of TBAF. The organic halide can be any organic halide known to a person skilled in the art which reacts with D-uronic acid. For example, the organic halide can have the formula Hal-R wherein R is defined as above. The halide can be, for example, Cl, Br or I.

The D-glucuronic benzyl ester 5b and the D-galacturonic benzyl ester (D-GalABn) 6b were prepared according to Stachulski et al. (SI) (E. R. Bowkett, J. R. Harding, J. L. Maggs, B. K. Park, J. A. Perrie and A. V. Stachulski, Tetrahedron, 2007, 63, 7596-7605). The esters 5b and 6b were fructosylated by the levansucrase of B. megaterium (SacB) leading to the sucrose esters β-D-fructofuranosyl-(2,1)-α-D-glucuronic acid benzyl ester 2b (45%) and 3-D-fructofuranosyl-(2,1)-α-D-galacturonic acid benzyl ester 3b (41%) (FIG. 5). The reactions were carried out at 37° C. in a 50 mm phosphate buffer with an enzyme activity of 2 U/mL. Both esters can be hydrolyzed with 1 M NaOH resulting in sucrose acids (SI).

A more sterically demanding molecule D-glucuronic acid iso-propyl ester (D-GlcAiPr) 5c was successfully recognized as acceptor by the levansucrase. Its fructosylation was performed in the same way as for D-GlcABn 5b leading to the formation of β-D-fructofuranosyl-(2,1)-α-D-glucuronic acid isopropyl ester 2c in 52% yield, respectively.

Scheme 2

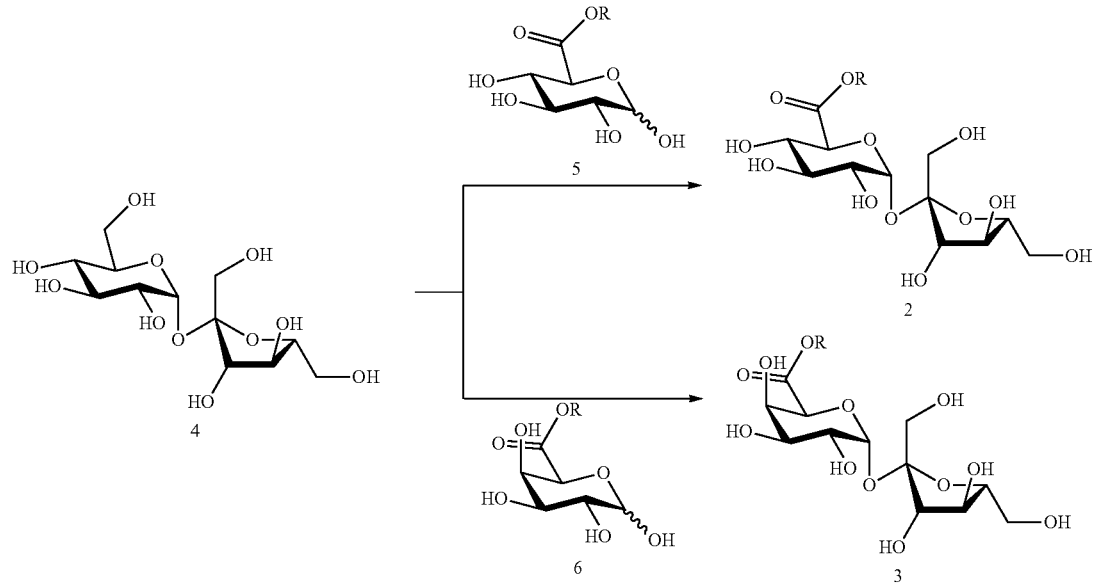

| | acceptor | product | yield |
|---|---|---|---|
| R = H | 5a | 2a | 43% |
| R = Bn | 5b | 2b | 45% |
| R = iPr | 5c | 2c | 52% |
| R = H | 6a | 3a | 40% |
| R = Bn | 6b | 3b | 41% |

The above yields were obtained using 1 M of 5 or 6, 0.5 M sucrose, 50 mm phosphate buffer pH 6.6, levansucrase SacB 2 U/mL, 2 h.

Also 6-tosyl and 6-azido-sucrose can be generated (Scheme 3). 6-tosylglucose needs to incubate with the levansucrase in buffer with sucrose. The reaction mixture should stir till the product is formed in sufficient yields. The progress of the reaction can be followed by thin layer chromatography. The mixture can be applied to column chromatography with silica. The product will be separated with the eluent (water/isopropanol/acidic acid ethylester=1: 3:6). The 6-tosyl sucrose can be transformed to 6-Azido sucrose.

Scheme 3

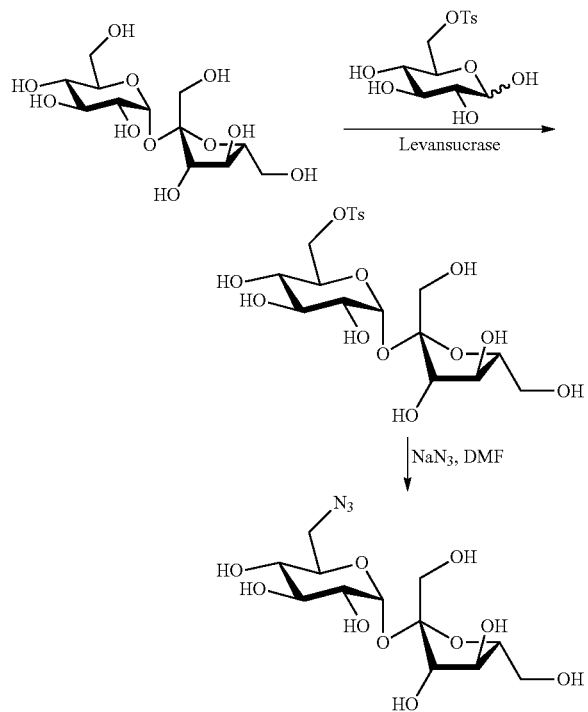

EXAMPLES

Figure 1:
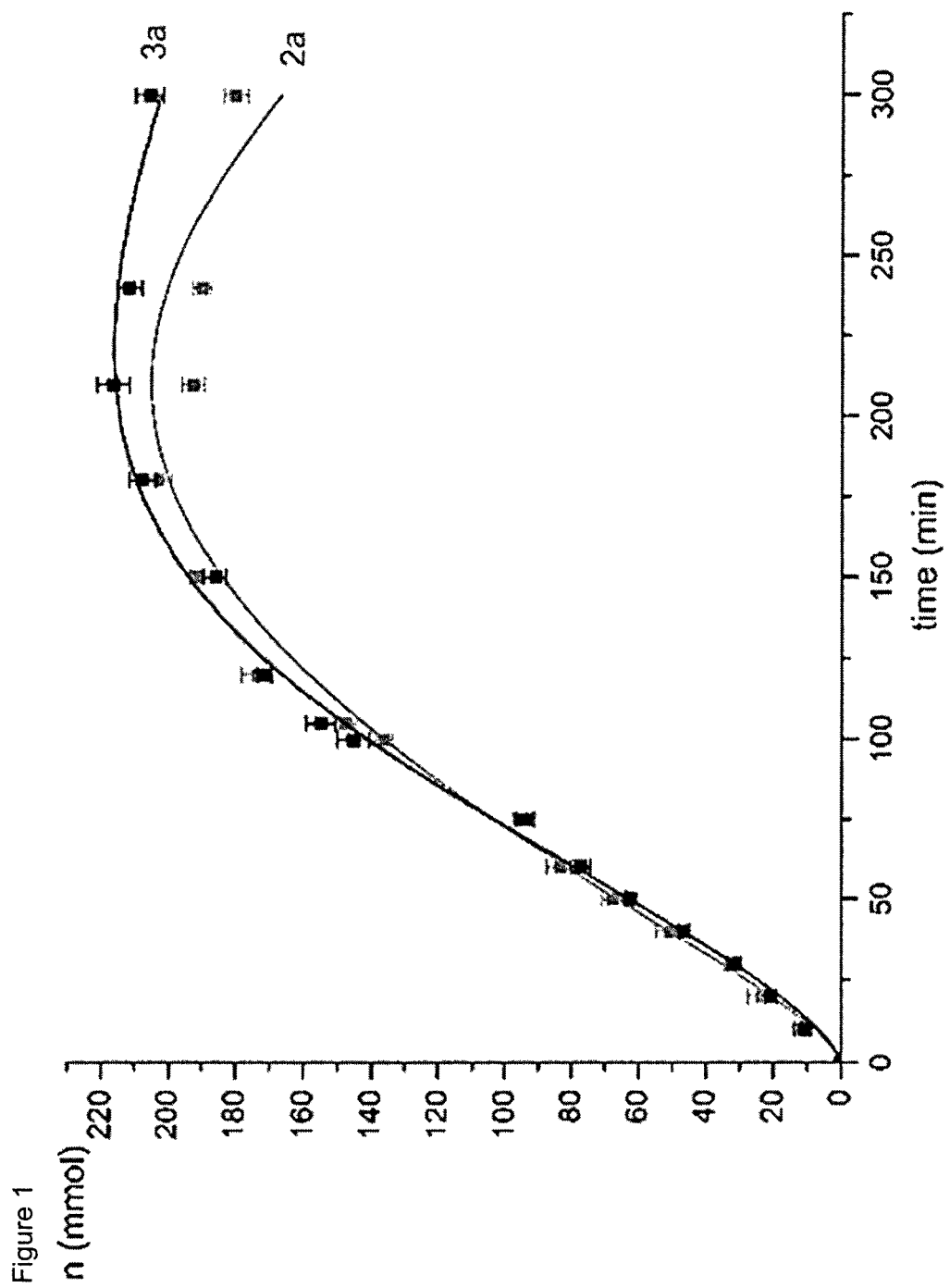
FIG. 1 the determined yields of fructosylated uronic acids (D-GlcAFru 2a, D-GalAFru 3a) via HPAEC. 0.7 M uronic acid, 0.35 M sucrose, 50 mm phosphate buffer pH 6.6 and 5% DMSO, 2 U/mL Bm-Ls.
Figure 2:
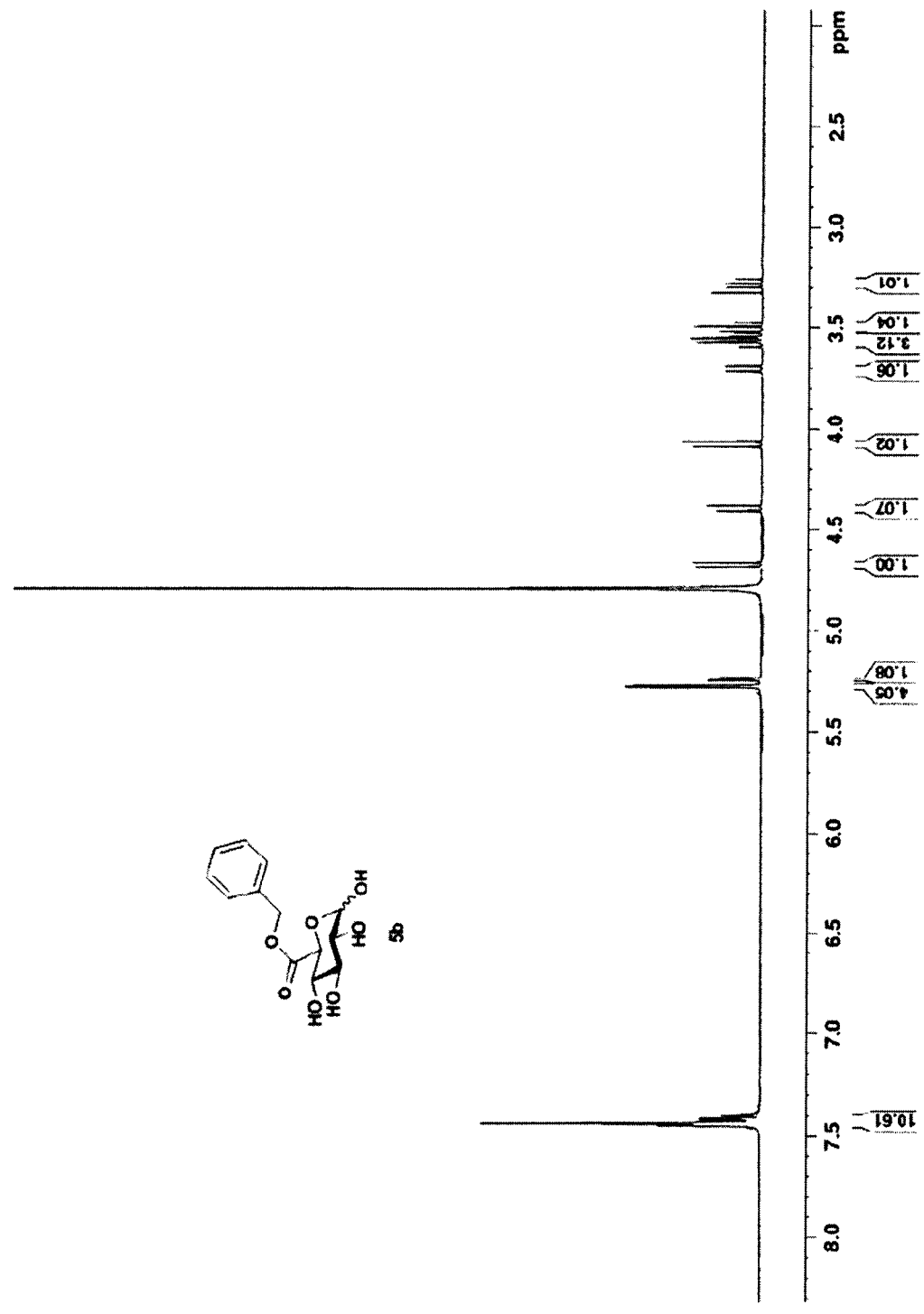
FIG. 2 shows the $^1$H-spectrum of D-glucuronic acid benzyl ester (5b) in D$_2$O/MeOD (400 MHz)
Figure 3:
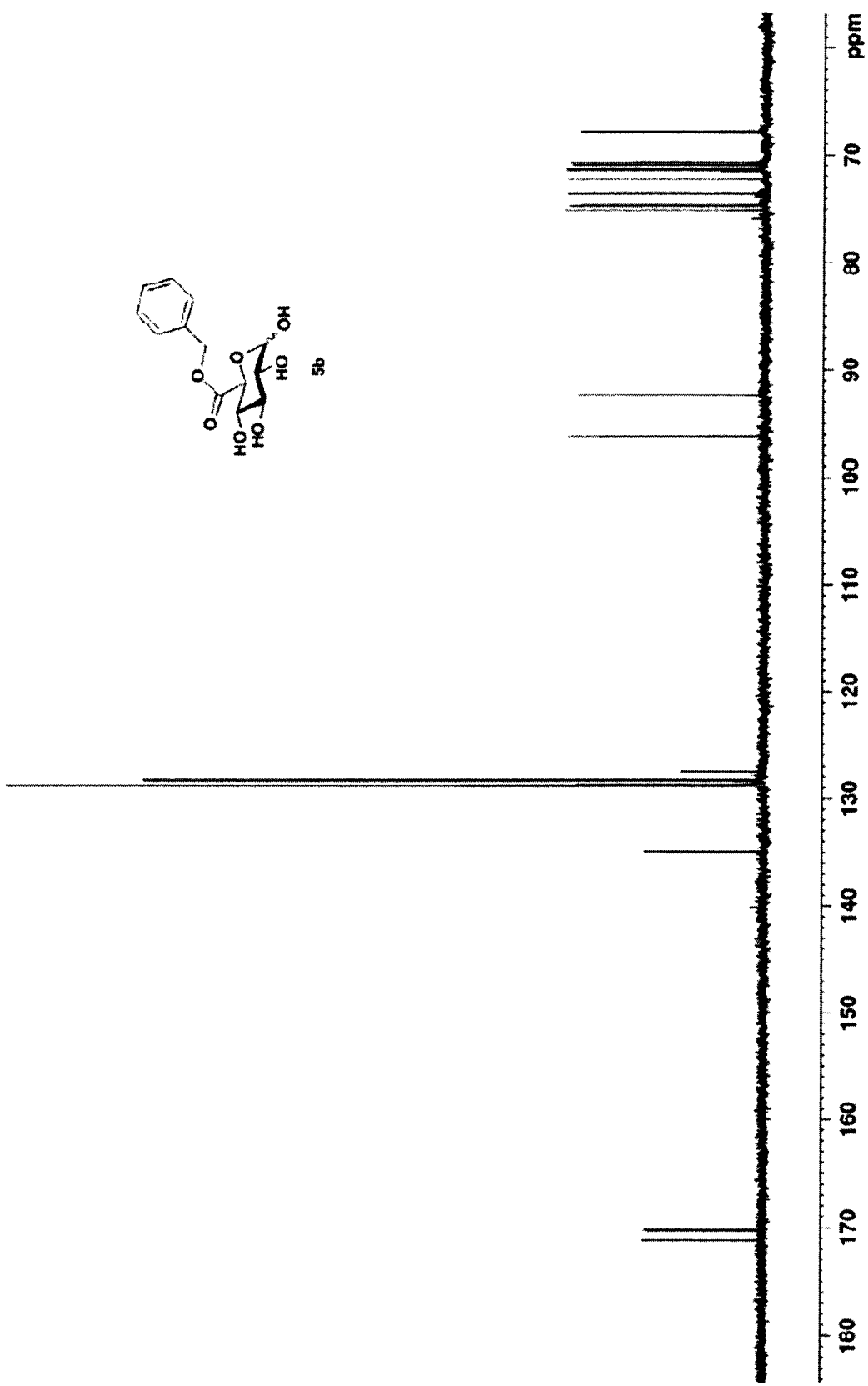
FIG. 3 shows the $^{13}$C-spectrum of D-glucuronic acid benzyl ester (5b) in D$_2$O/MeOD (101 MHz)
Figure 4:
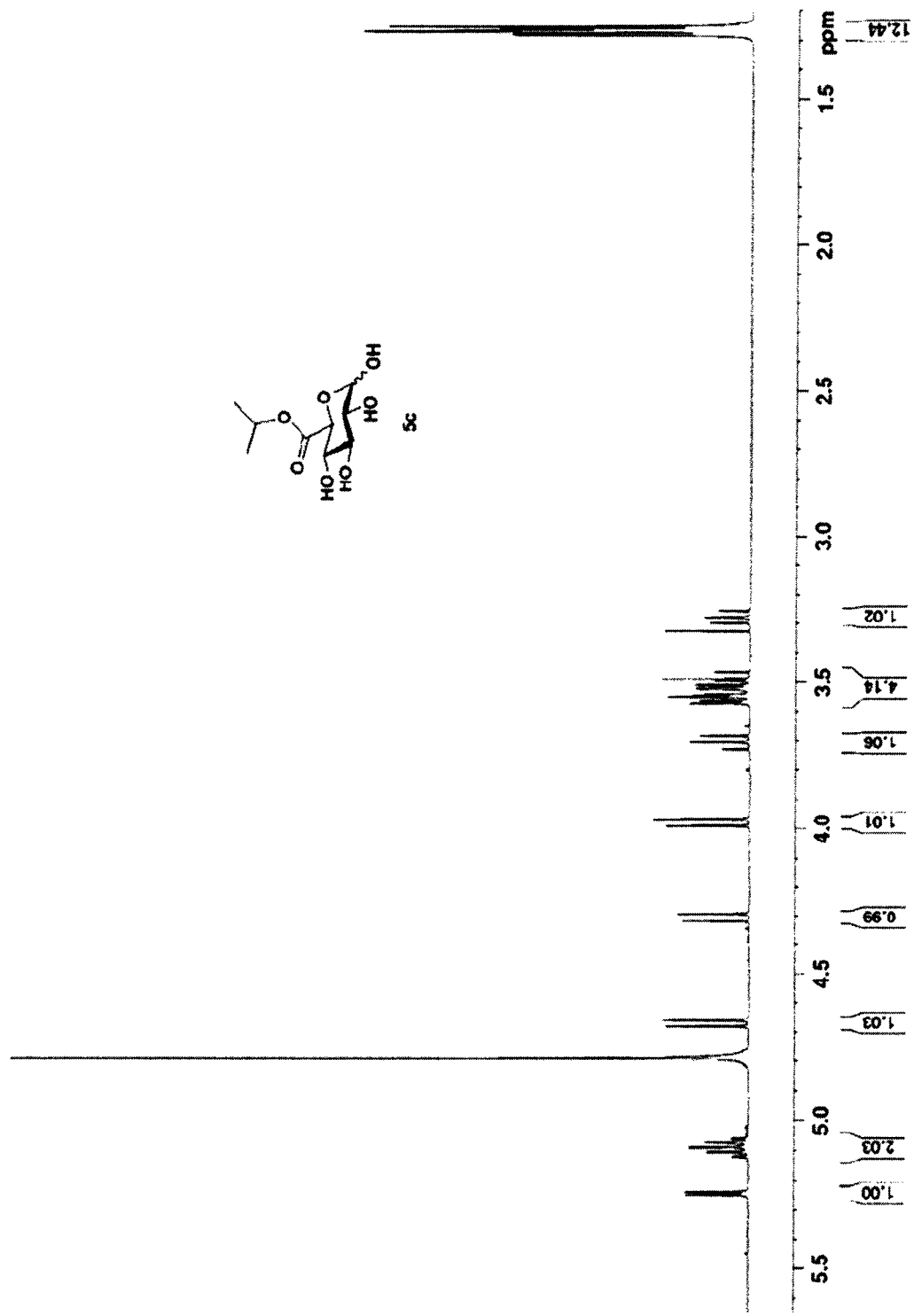
FIG. 4 shows the $^1$H-spectrum of D-glucuronic acid iso-propyl ester (5c) in D$_2$O/MeOD (400 MHz)
Figure 5:
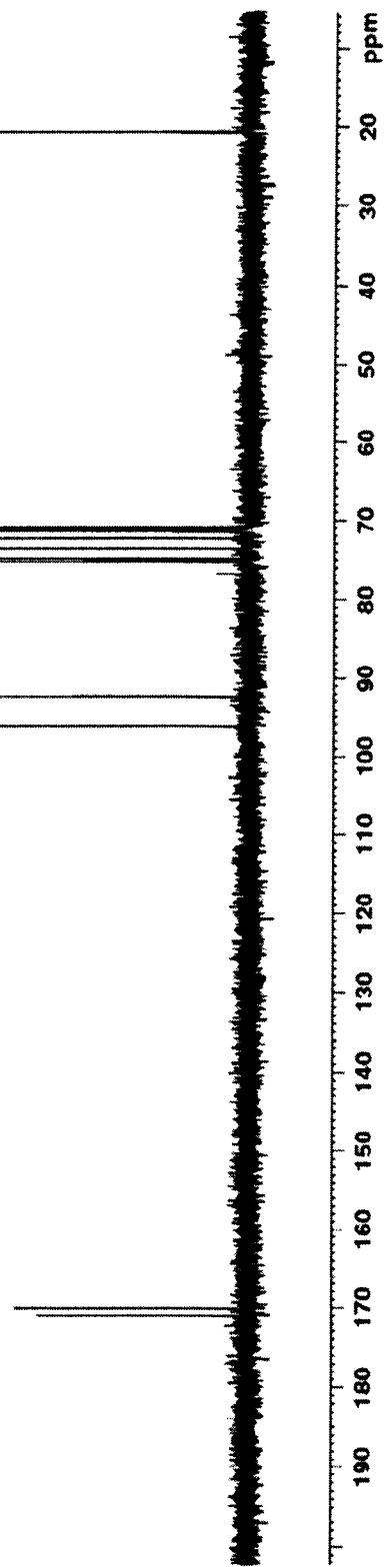
FIG. 5 shows the $^{13}$C-spectrum of D-glucuronic acid iso-propyl ester (5c) in D$_2$O/MeOD (101 MHz)
Figure 6:
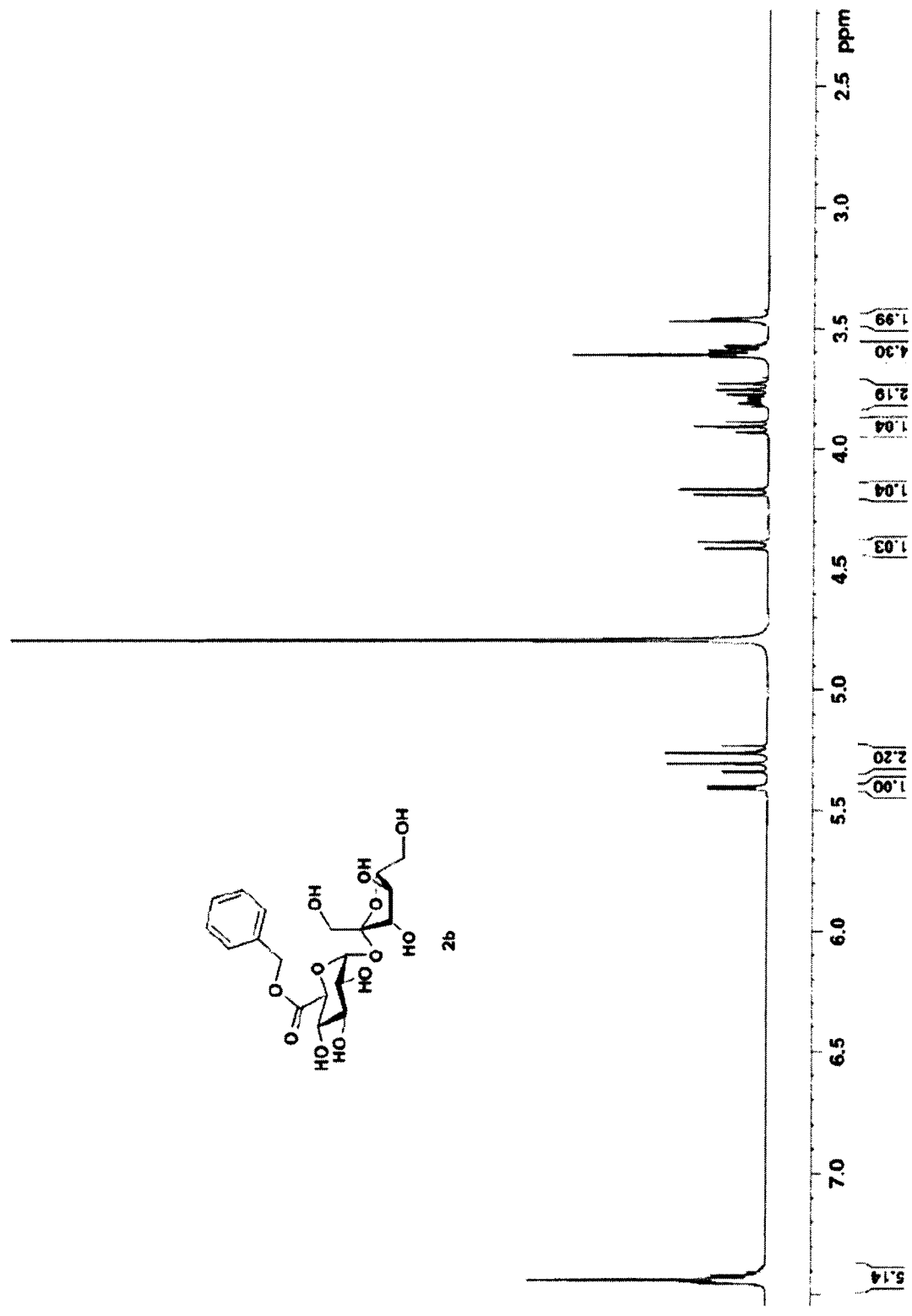
FIG. 6 shows the $^1$H-spectrum of β-D-fructofuranosyl-α-D-glucuronic acid benzyl ester (2b) in D$_2$O/MeOD (400 MHz)
Figure 7:
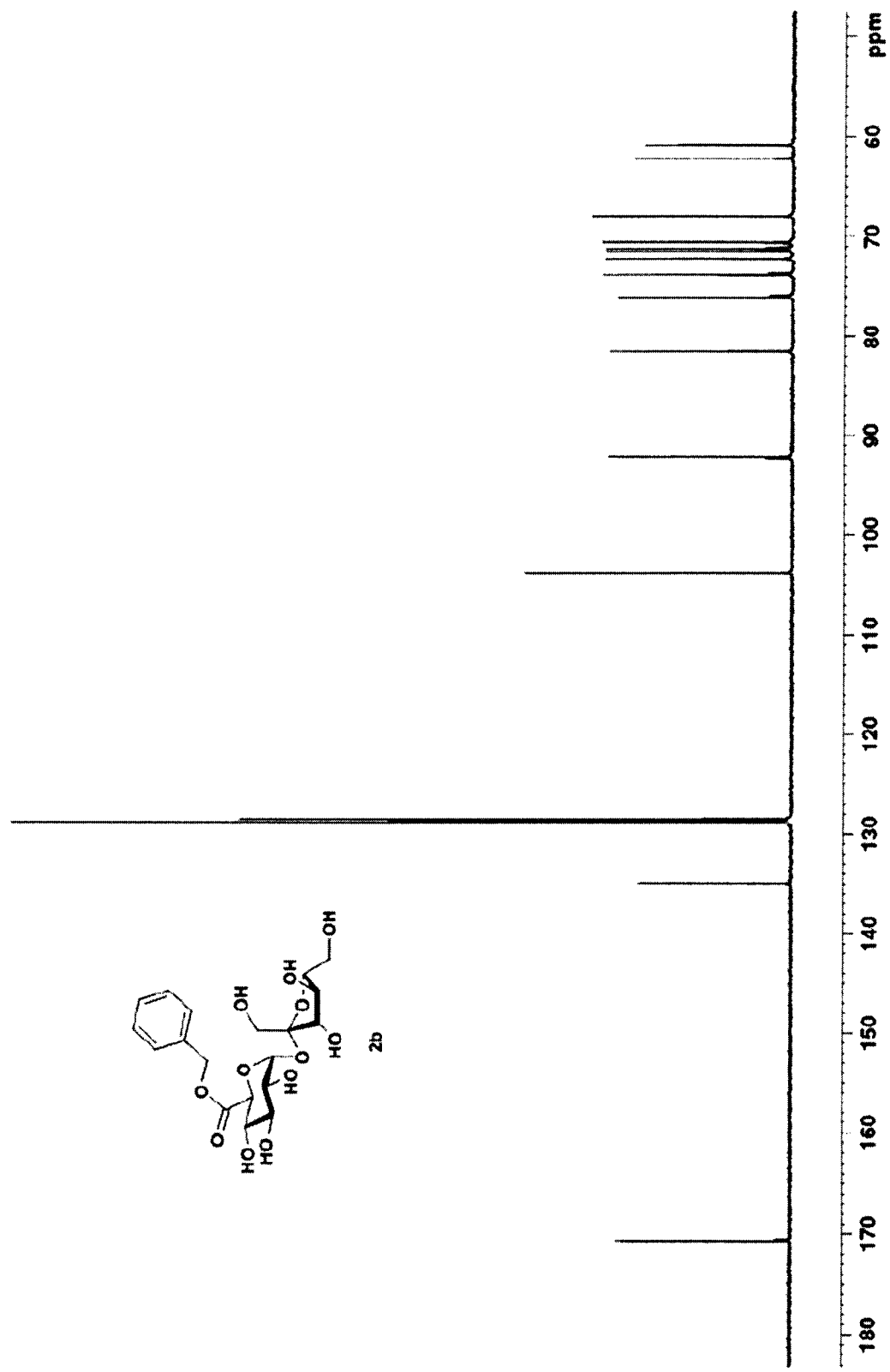
FIG. 7 shows the $^{13}$C-spectrum of β-D-fructofuranosyl-α-D-glucuronic acid benzyl ester (2b) in D$_2$O/MeOD (101 MHz)
Figure 8:
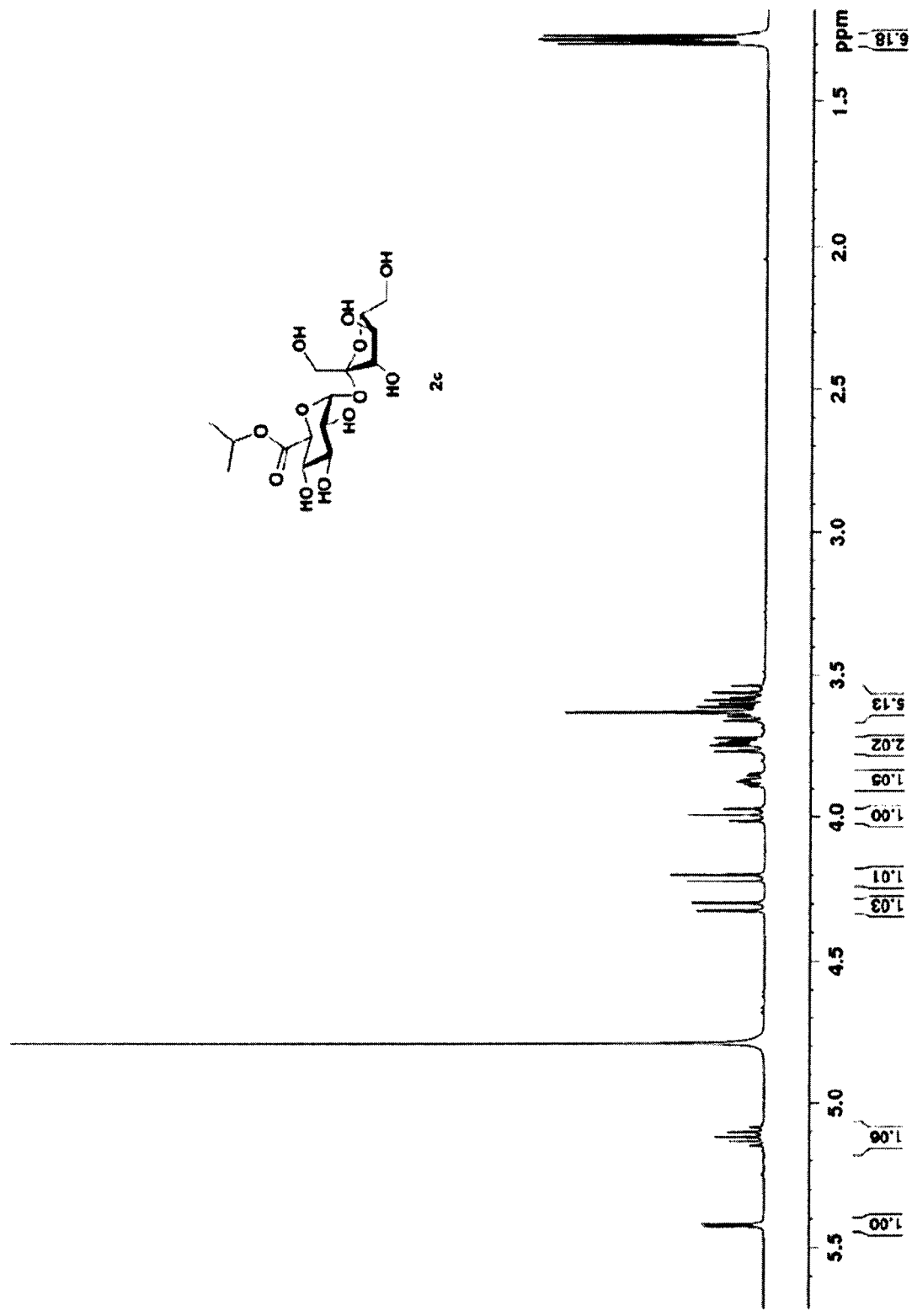
FIG. 8 shows the $^1$H-spectrum of β-D-fructofuranosyl-α-D-glucuronic acid iso-propyl ester (2c) in D$_2$O/MeOD (400 MHz)
Figure 9:
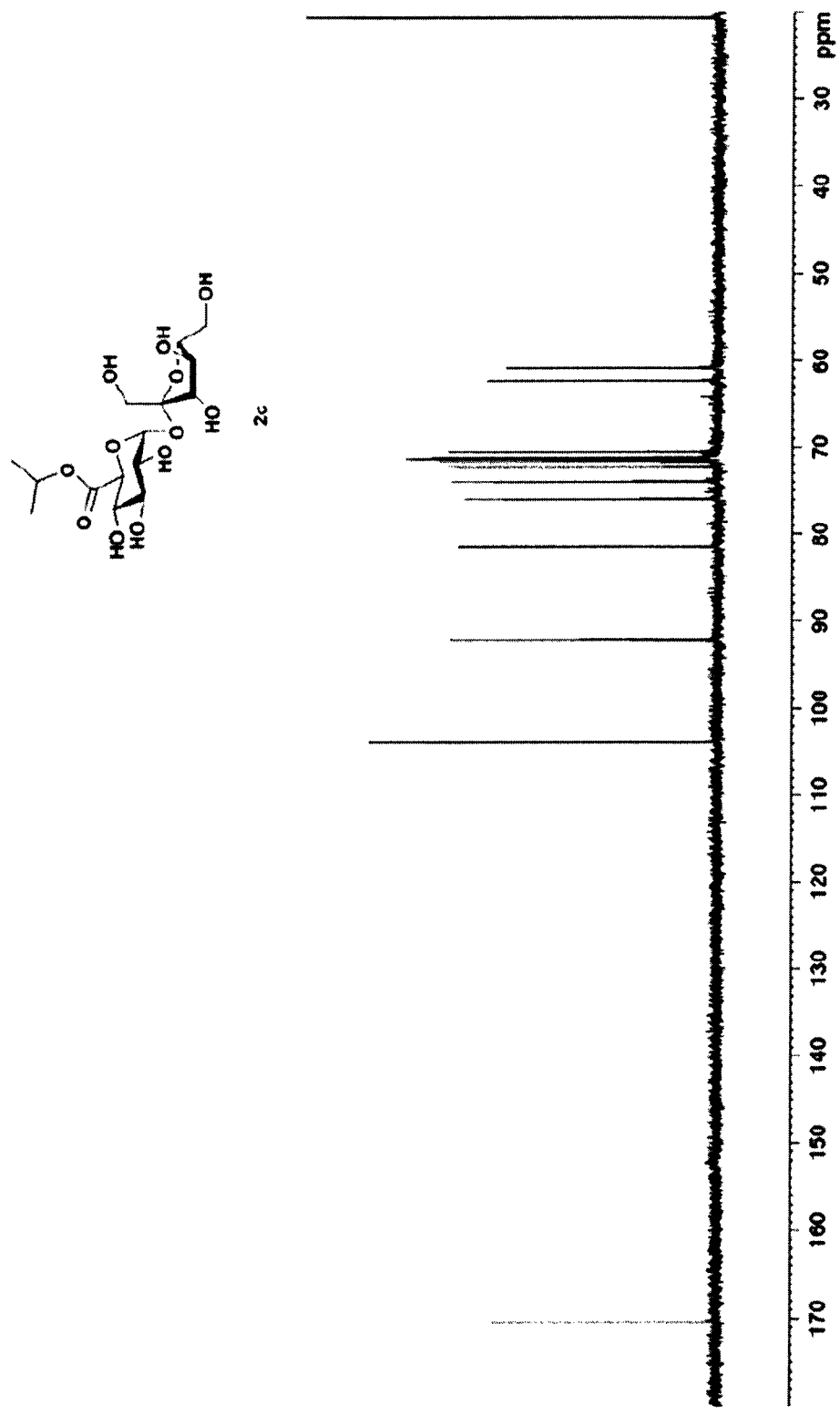
FIG. 9 shows the $^{13}$C-spectrum of β-D-fructofuranosyl-α-D-glucuronic acid iso-propyl ester (2c) in D$_2$O/MeOD (101 MHz)
Figure 10:
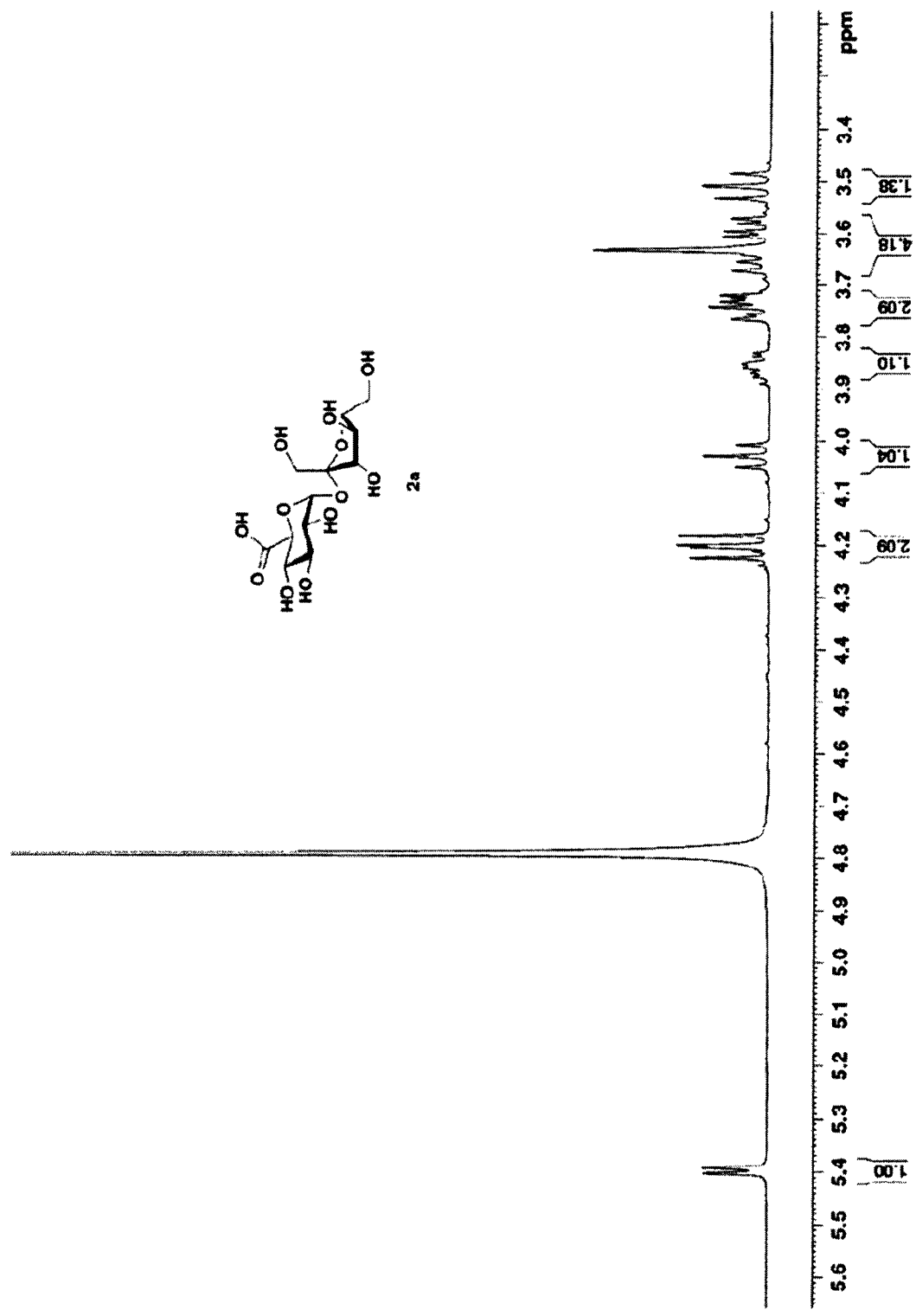
FIG. 10 shows the $^1$H-spectrum of β-D-fructofuranosyl-α-D-glucuronic acid (2a) in D$_2$O/MeOD (400 MHz)
Figure 11:
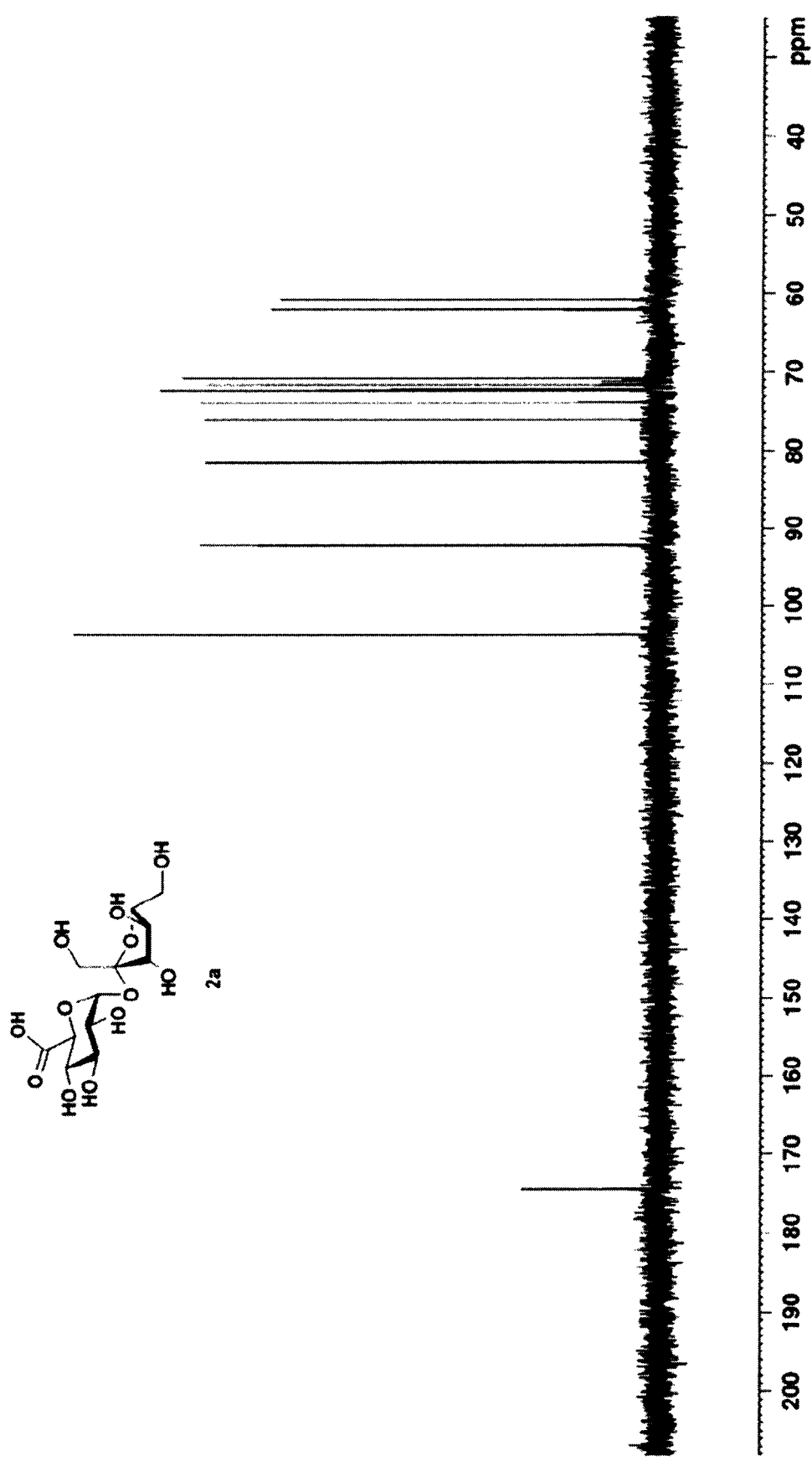
FIG. 11 shows the $^{13}$C-spectrum of β-D-fructofuranosyl-α-D-glucuronic acid (2a) in D$_2$O/MeOD (101 MHz)
Figure 12:
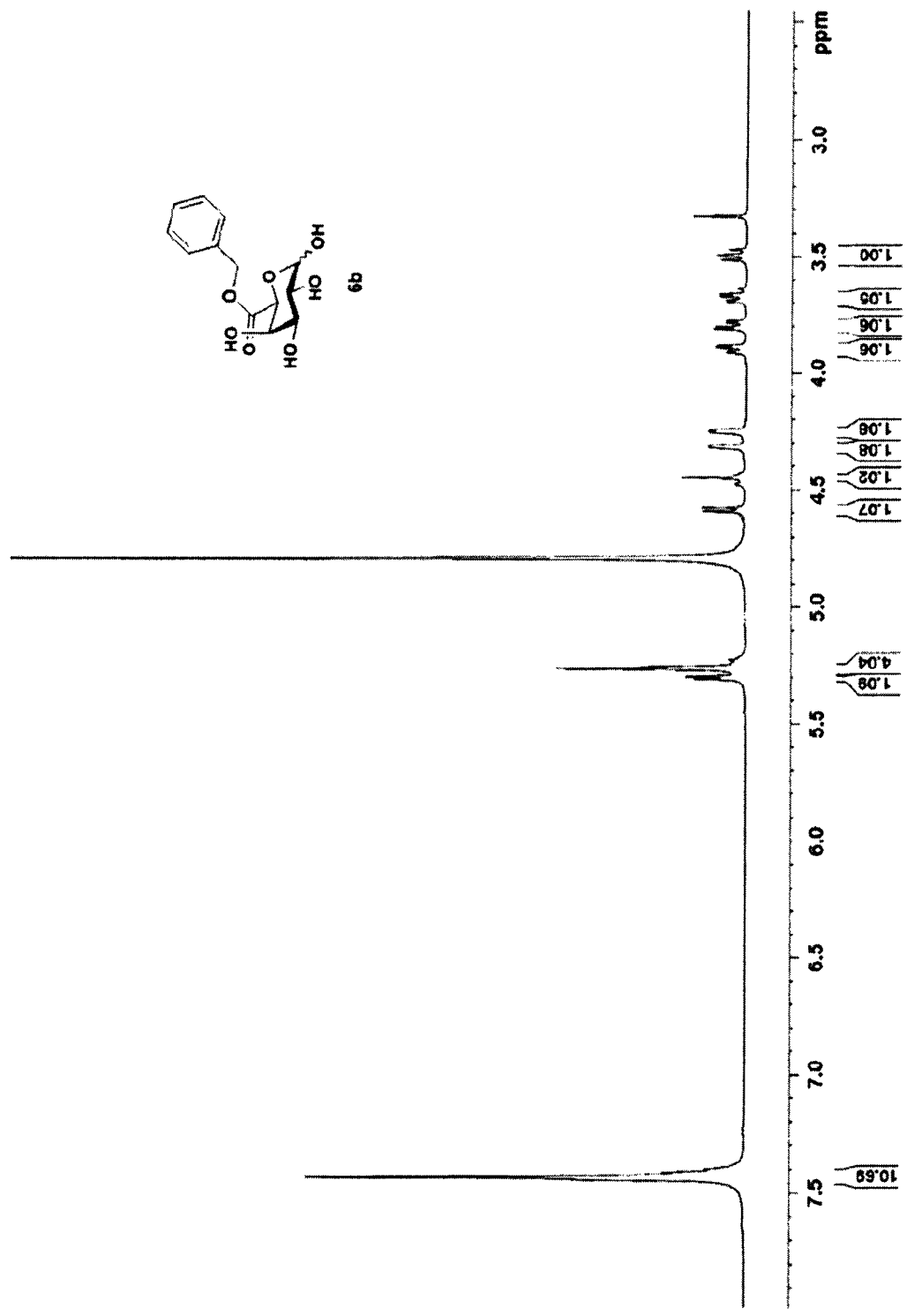
FIG. 12 shows the $^1$H-spectrum of D-galacturonic acid benzyl ester (6b) in D$_2$O/MeOD (400 MHz)
Figure 13:
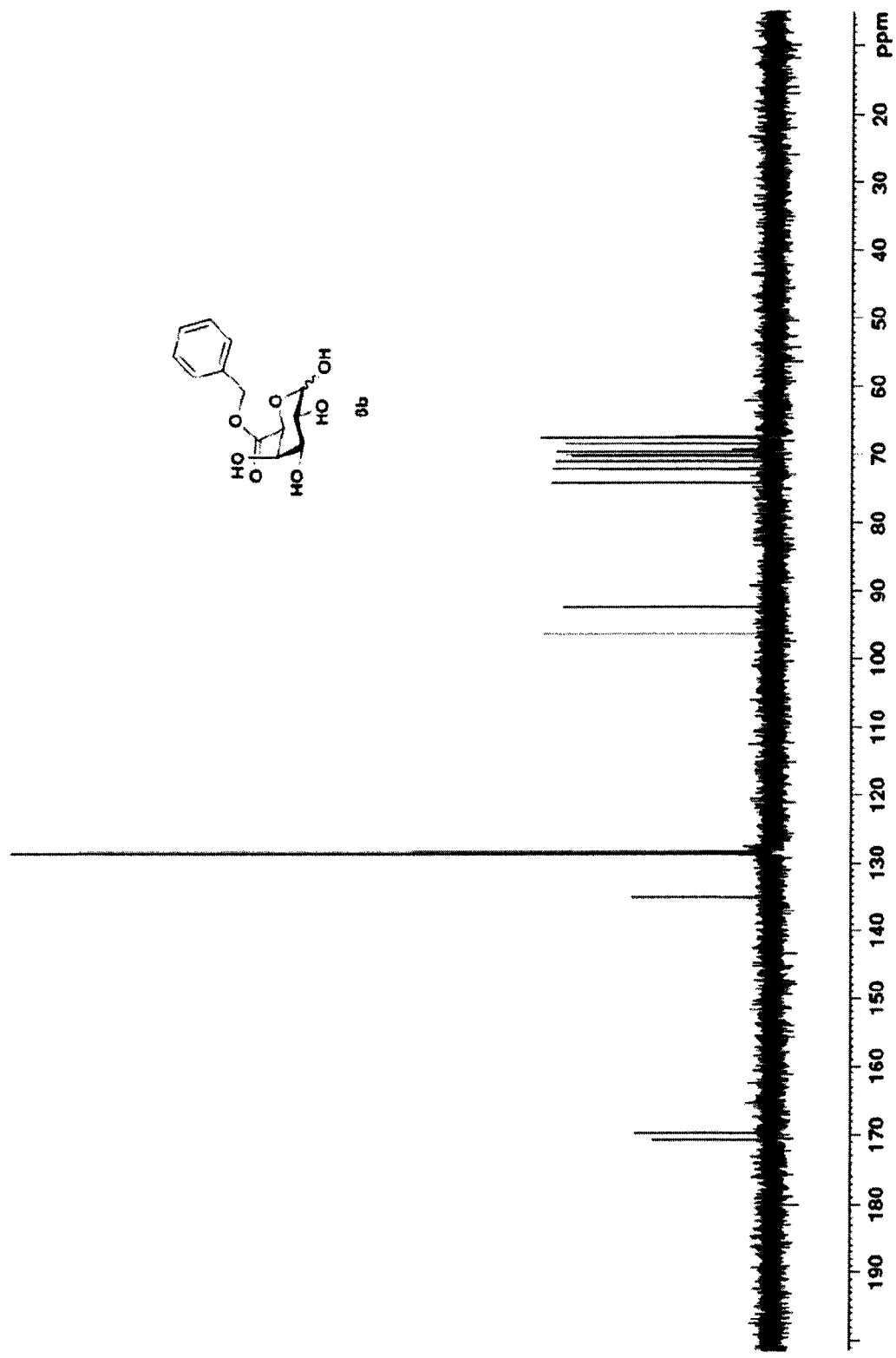
FIG. 13 shows the $^{13}$C-spectrum of D-galacturonic acid benzyl ester (6b) in D$_2$O/MeOD (101 MHz)
Figure 14:
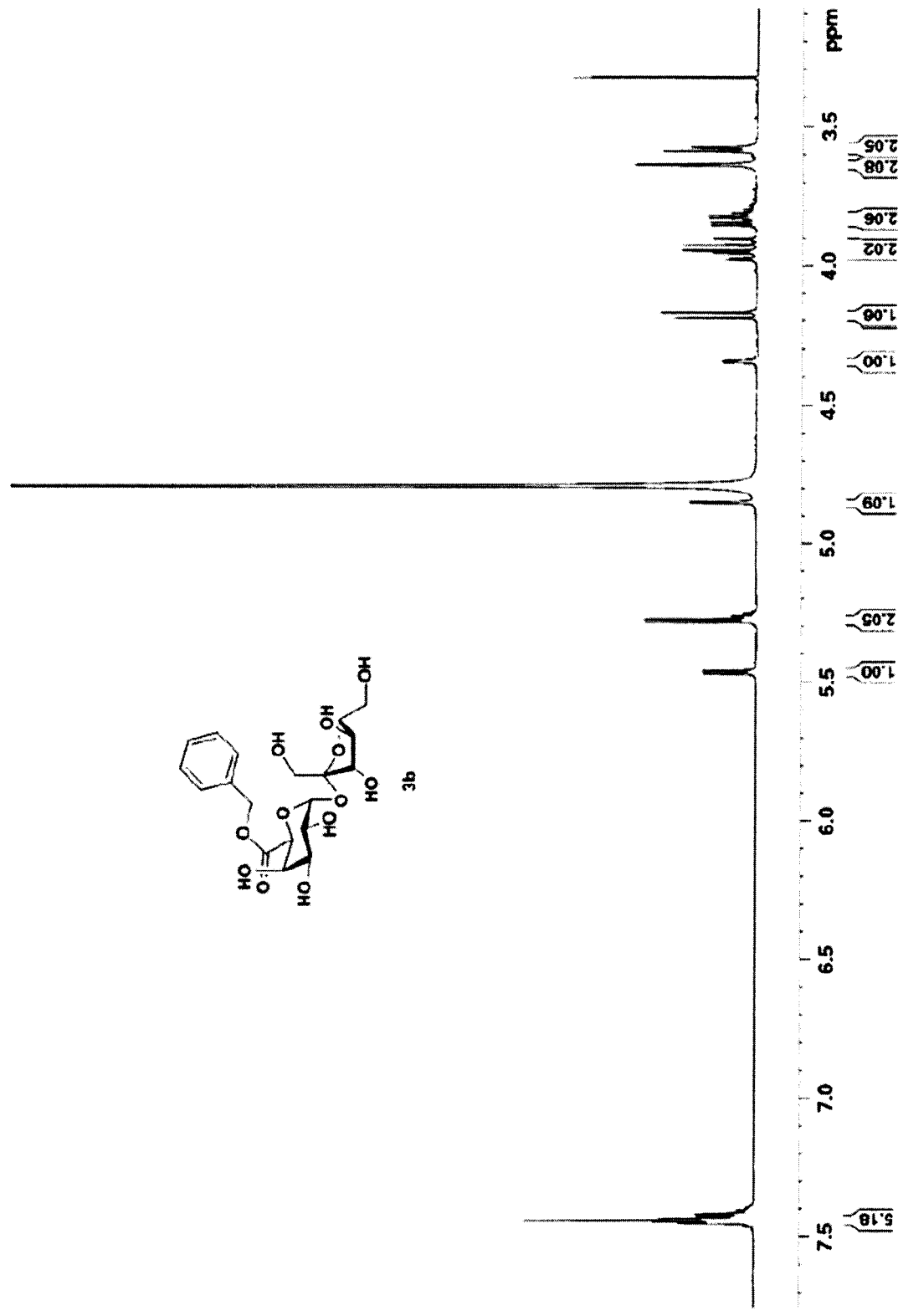
FIG. 14 shows the $^1$H-spectrum of β-D-fructofuranosyl-α-D-galacturonic acid benzyl ester (3b) in D$_2$O/MeOD (400 MHz)
Figure 15:
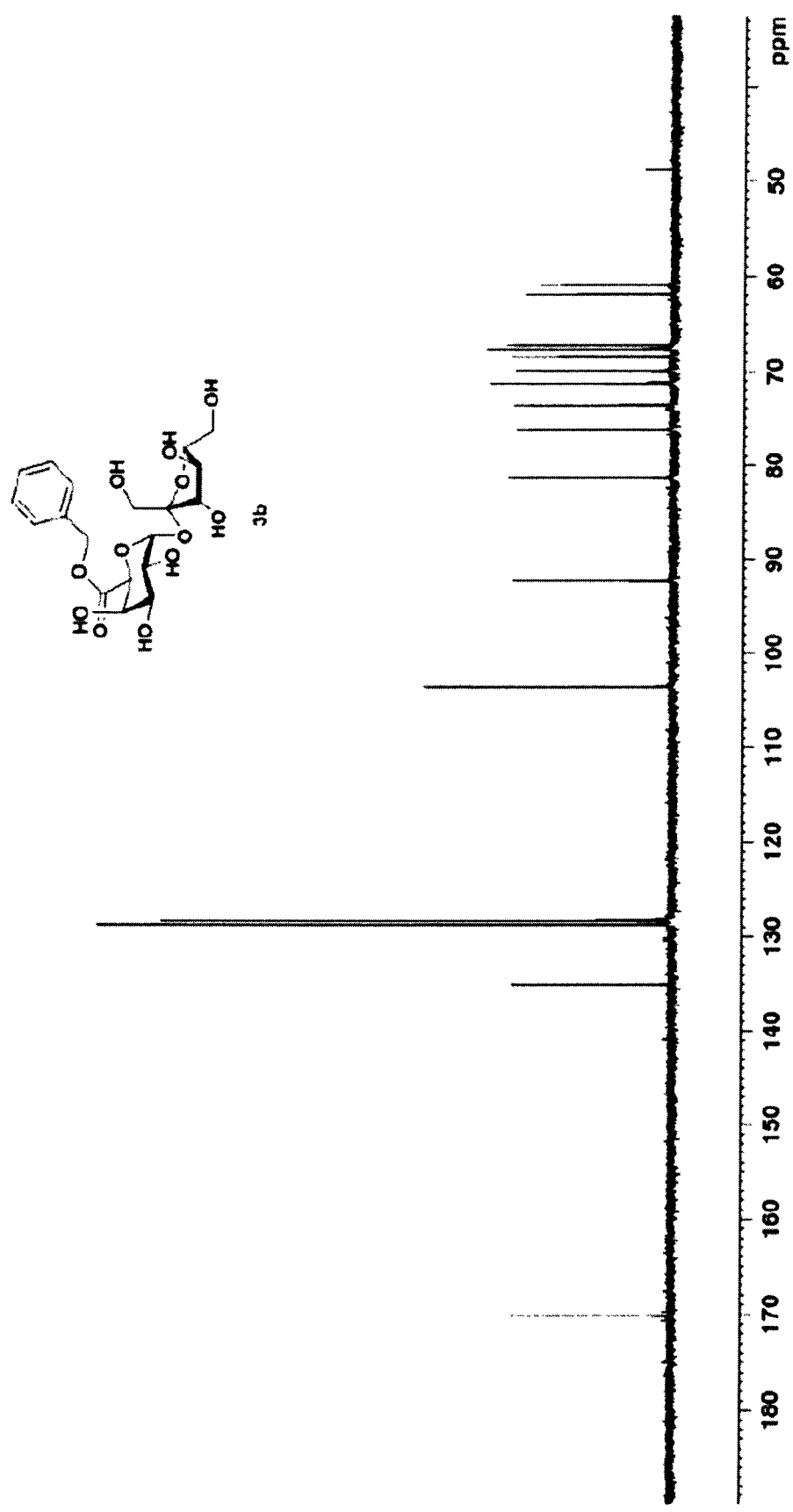
FIG. 15 shows the $^{13}$C-spectrum of β-D-fructofuranosyl-α-D-galacturonic acid benzyl ester (3b) in D$_2$O/MeOD (101 MHz)
Figure 16:
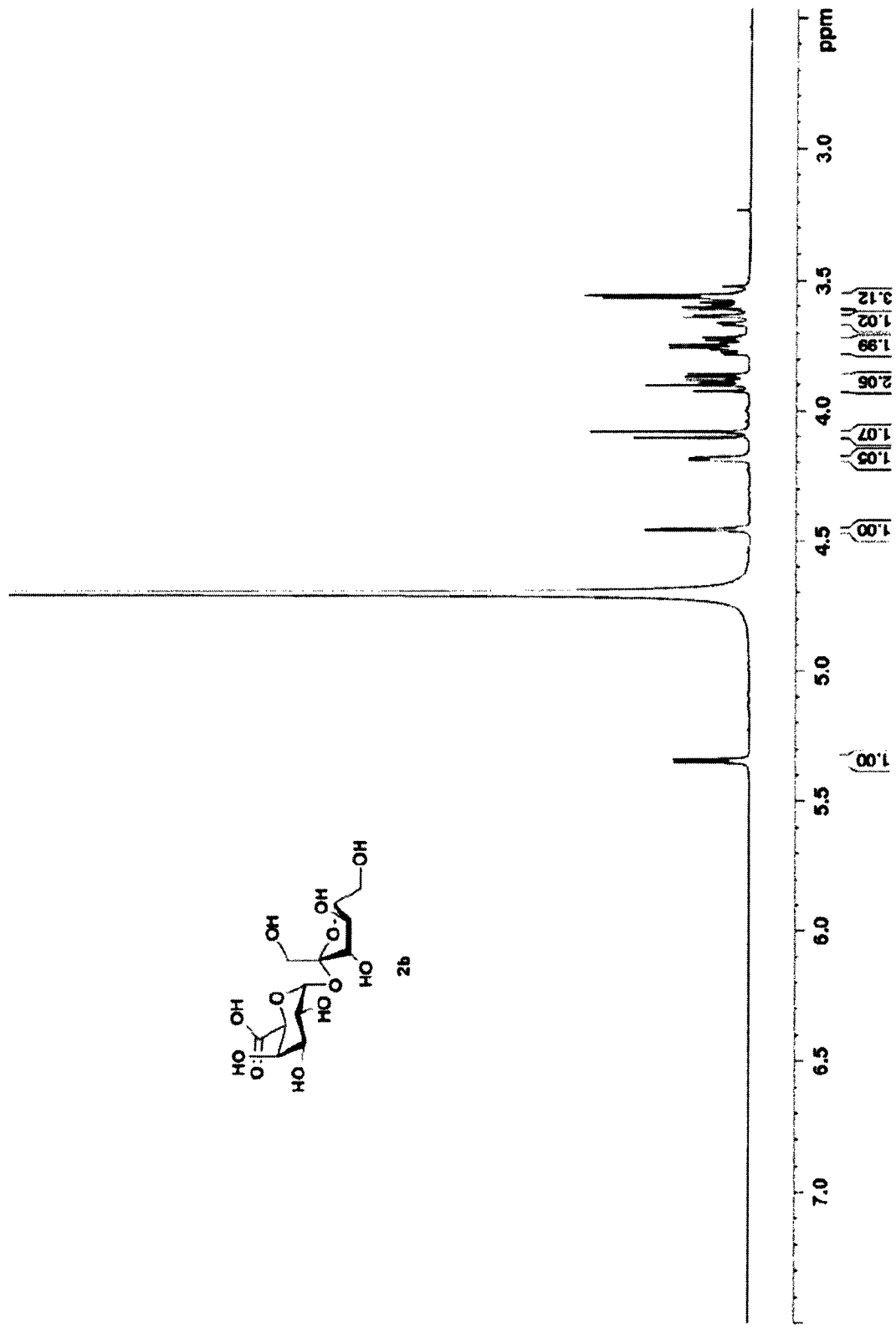
FIG. 16 shows the $^1$H-spectrum of β-D-fructofuranosyl-α-D-galacturonic acid (3a) in D$_2$O/MeOD (400 MHz)
Figure 17:
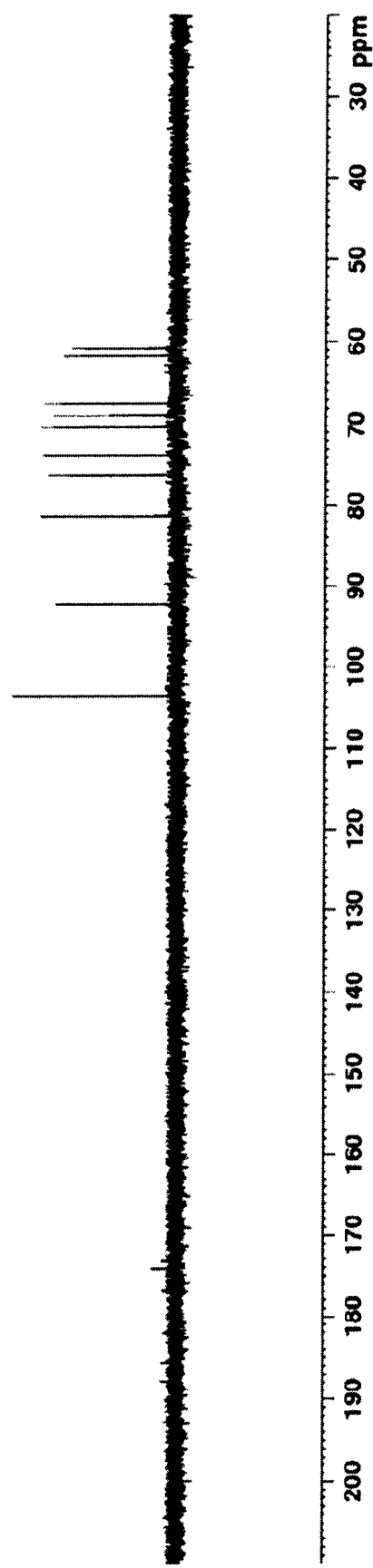
FIG. 17 shows the $^{13}$C-spectrum of β-D-fructofuranosyl-α-D-galacturonic acid (3a) in D$_2$O/MeOD (101 MHz)
Figure 17:
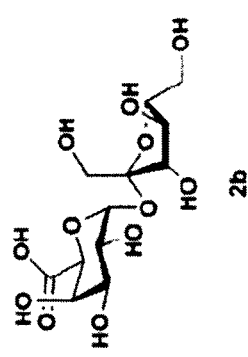
Figure 18:
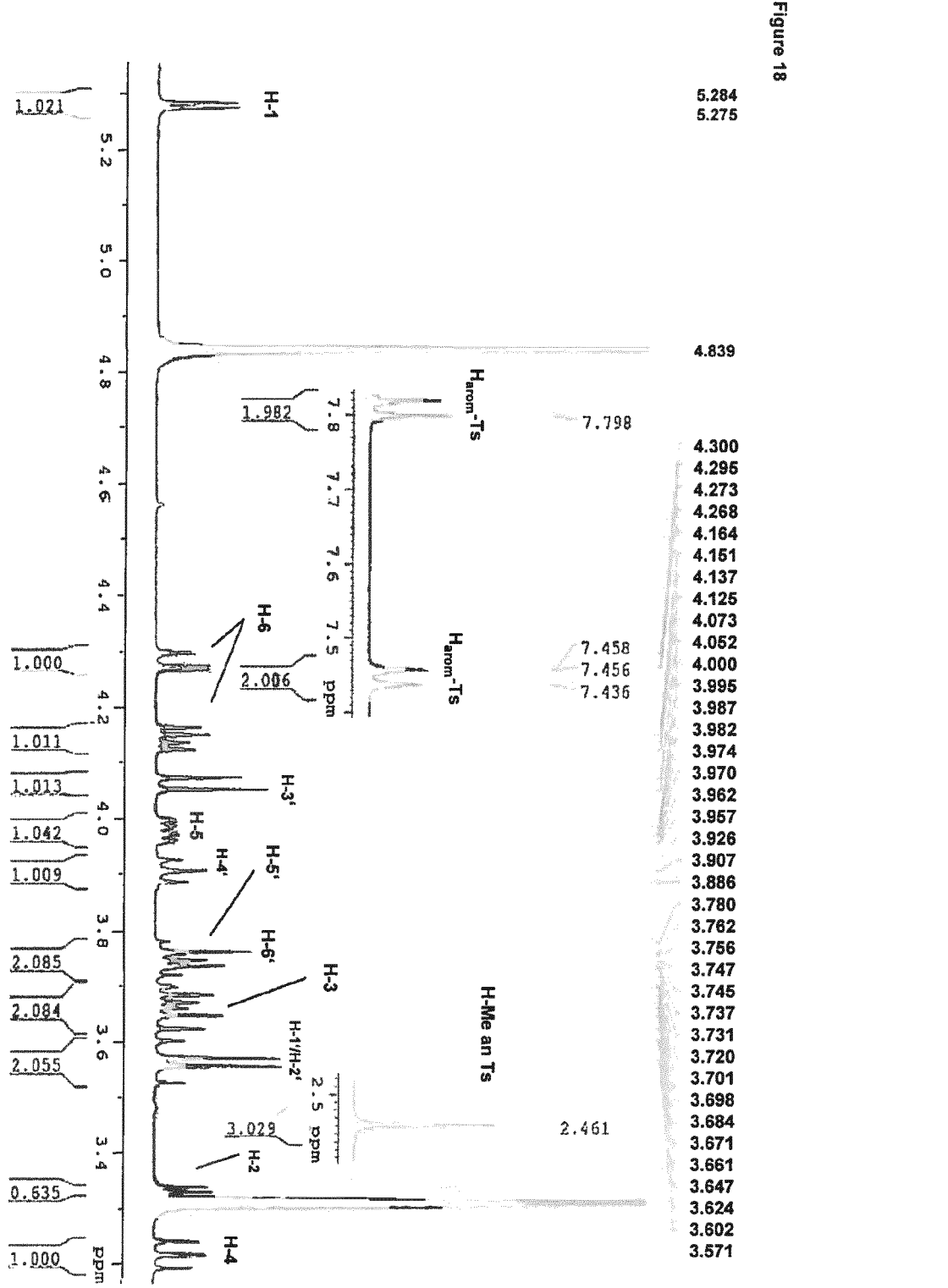
FIG. 18 shows the $^1$H-spectrum of 6-O-Toluolsulfonyl-D-glucopyranosyl-β-D-fructofuranoside in D$_2$O/MeOD (400 MHz)
Figure 19:
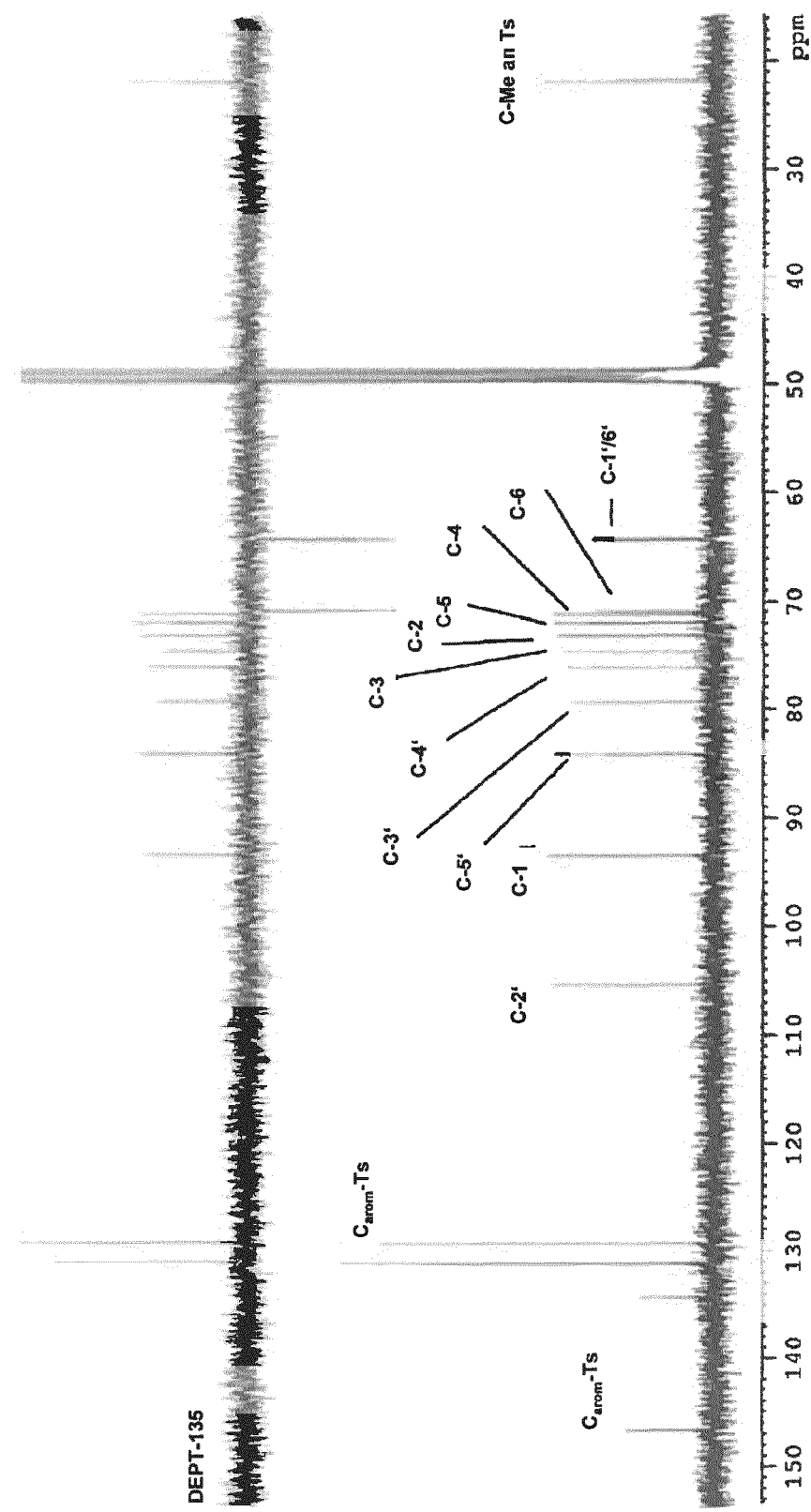
FIG. 19 shows the $^{13}$C-spectrum of 6-O-Toluolsulfonyl-D-glucopyranosyl-β-D-fructofuranoside in D$_2$O/MeOD (100 MHz)
Figure 20:
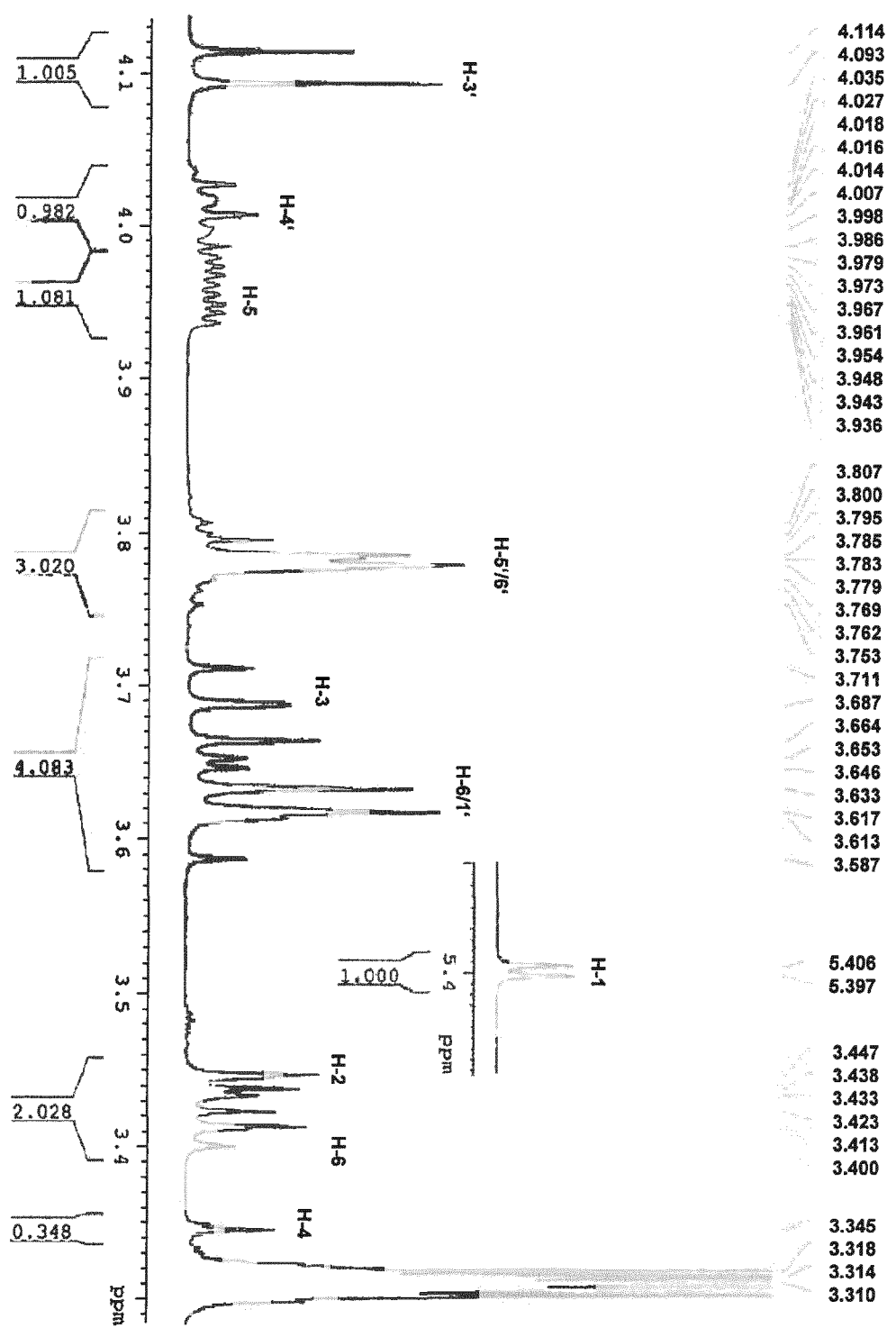
FIG. 20 shows the $^1$H-spectrum of 6-O-Azido-D-glucopyranosyl-β-D-fructofuranoside in D$_2$O/MeOD (400 MHz)
Figure 21:
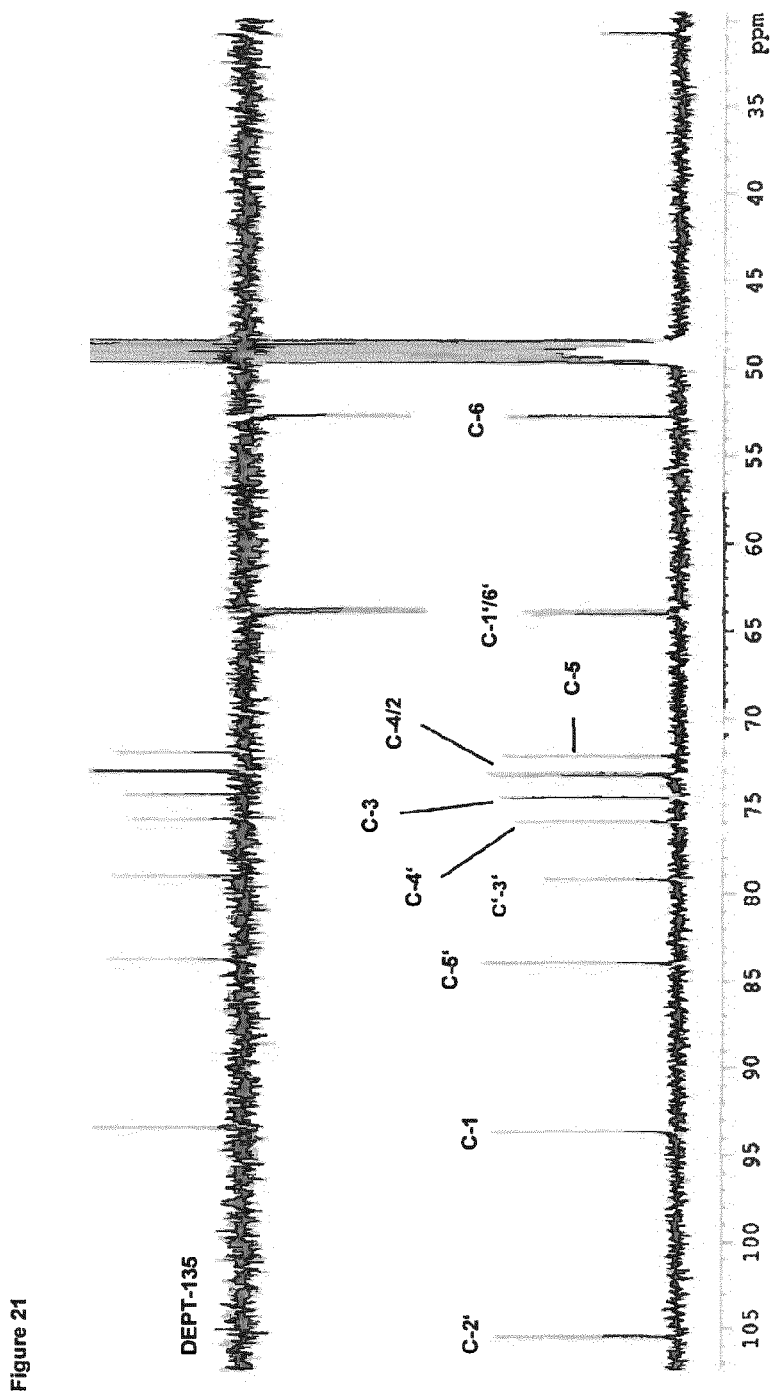
FIG. 21 shows the $^{13}$C-spectrum of 6-O-Azido-D-glucopyranosyl-β-D-fructofuranoside in D$_2$O/MeOD (100 MHz)
Figure 22:
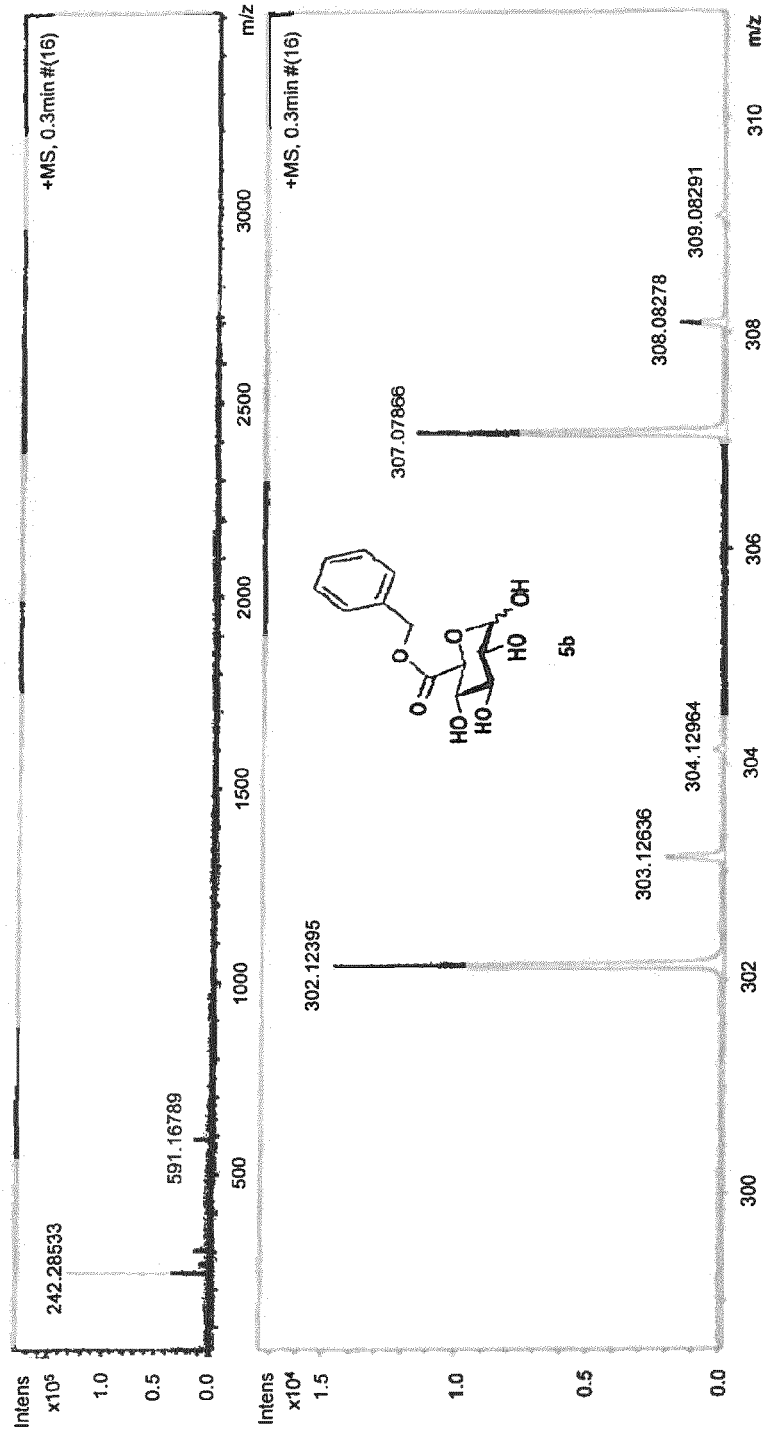
FIG. 22 shows the HRMS (ESI pos.) of D-glucuronic acid benzylic ester (5b)
Figure 23:
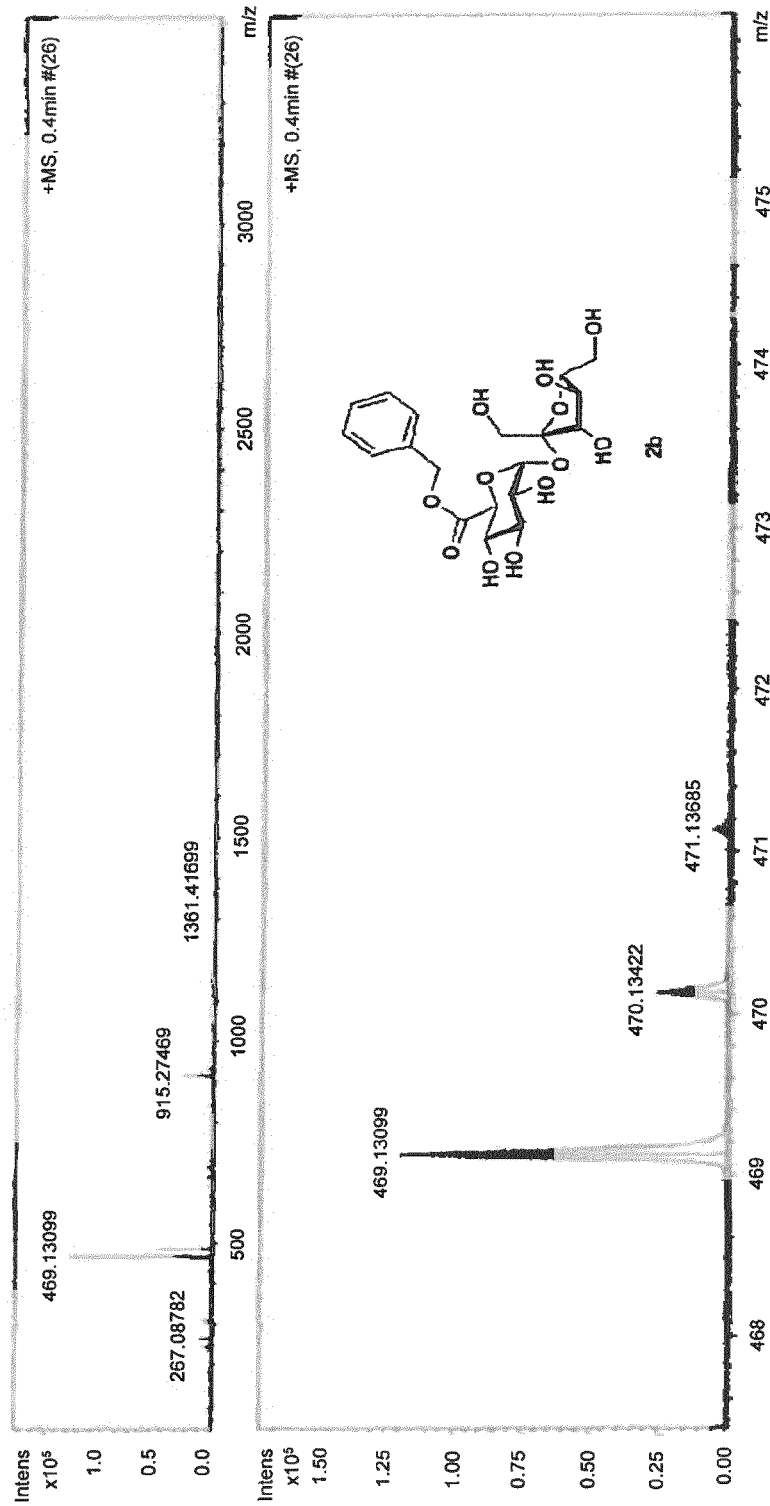
FIG. 23 shows the HRMS (ESI pos.) of D-glucuronic acid benzylic ester (2b)
Figure 24:
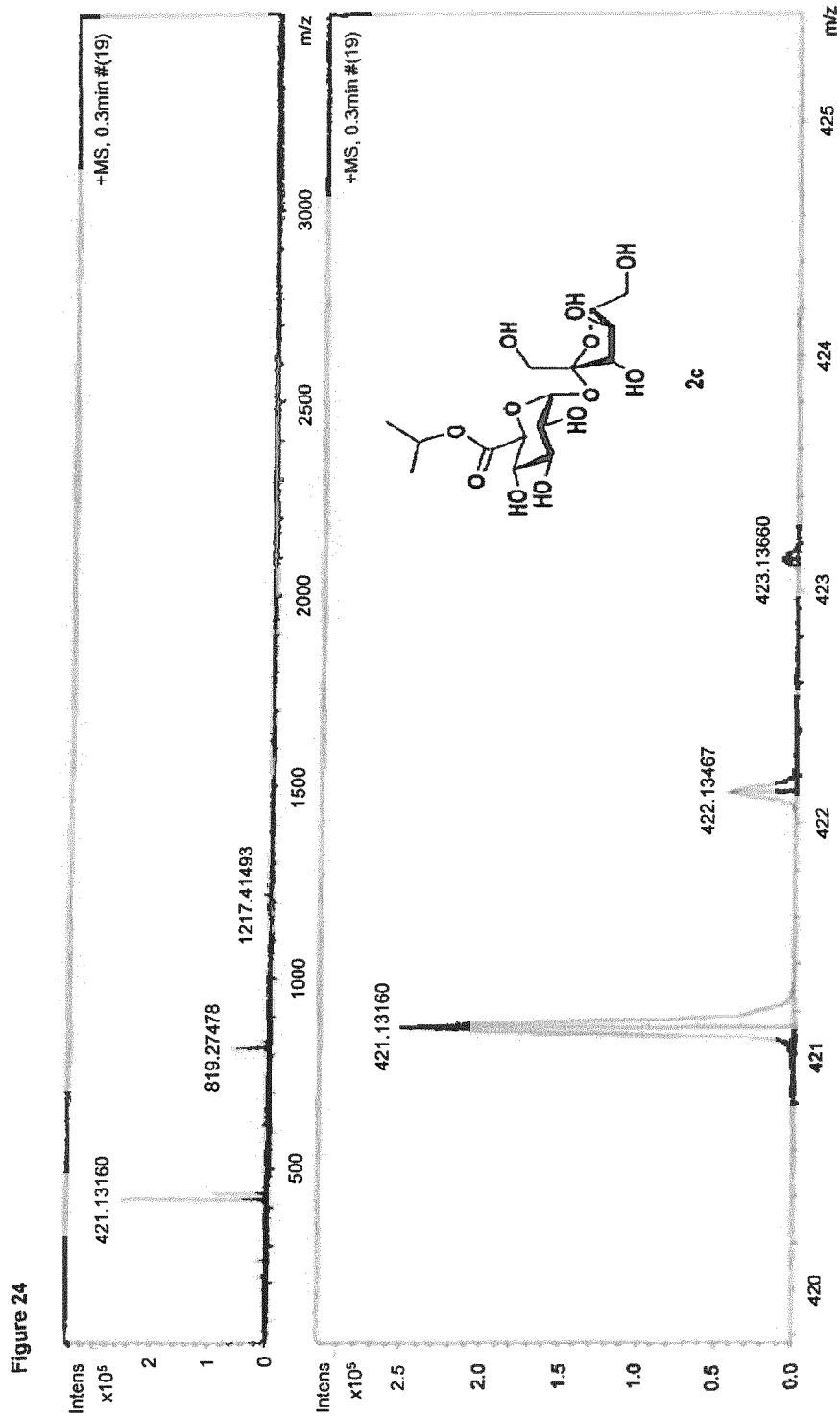
FIG. 24 shows the HRMS (ESI pos.) of β-D-fructofuranosyl-α-D-glucuronic acid iso-propylic ester (2c)
Figure 25:
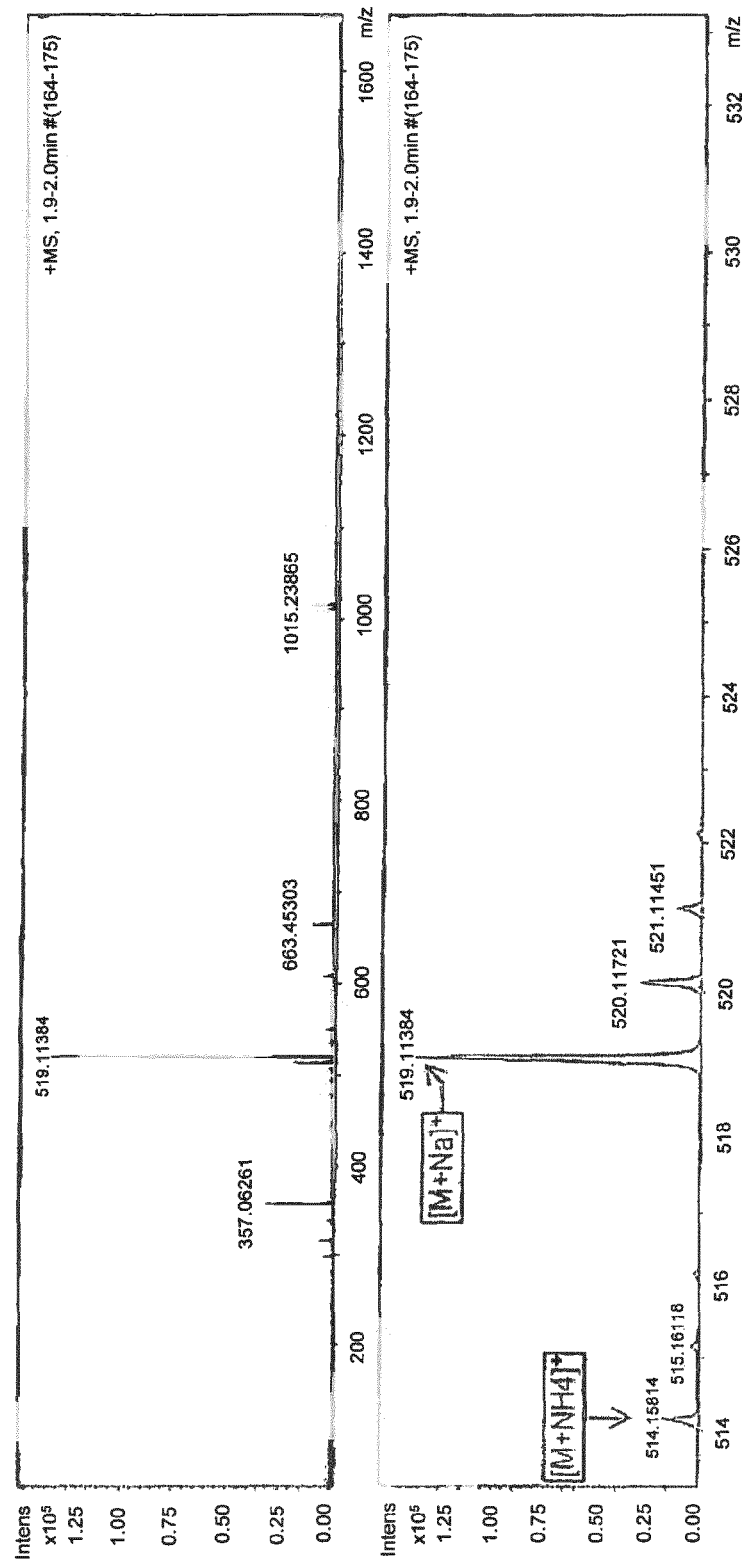
FIG. 25 shows the HRMS (ESI pos.) of 6-O-Toluolsulfonyl-D-glucopyranosyl-β-D-fructofuranoside.

Chemicals were purchased from commercial sources (Sigma Aldrich, VWR Chemicals, Carbosynth) and applied without further purification. Solvents were distilled prior to use. Deuterated solvents for NMR measurements were obtained from Deutero and used as received. NMR spectra were measured on a BRUKER AVANCE 400 FT-NMR at 25° C. Proton chemical shifts (δ scale) are expressed as parts per million (ppm) and were determined relative to a residual protic solvent as an internal reference (D$_2$O: δ=4.79 ppm, MeOD: δ=3.31 ppm). Data for $^1$H-NMR spectra are listed as follows: chemical shift (δ ppm) (multiplicity, integration, coupling constants (Hz), assigned proton). Couplings are indicated as: d=doublet, dd=doublet of doublet, ddd=doublet of doublet of doublet, m=multiplet. $^{13}$C-NMR spectra were recorded with the same BRUKER spectrometer at 100.9 MHz. Carbon chemical shifts (δ scale) are indicated in in parts per million (ppm) as well and calibrated to the carbon resonance of the respective solvent (MeOD: δ=49.00 ppm). Mass spectrometry (MS) measurements were performed on a BRUKER Daltonics autoflex//(electrospray ionization, ESI) instrument.

Experimental Section

Expression of *B. megaterium* levansucrase SacB

One single colony of freshly transformed *E. coli* bearing the selected plasmids was used to inoculate 10 mL LB-medium containing 10 µg/mL kanamycin. Precultures were incubated over night at 37° C. and used to inoculate 250 mL LB-medium with the appropriate antibiotic. Expression of the levansucrase SacB was induced when cells reached an $OD_{600}$ of around 0.6 by adding IPTG (isopropyl-β-D-thiogalactoside) at a final concentration of 0.5 mM. Cultures were incubated over night at 20° C. Cells were harvested by centrifugation and resuspended in 7 mL of 50 mM phosphate buffer pH 6.6. After sonication, the extracts were cleared by centrifugation at 13000×g.

Activity Assays of SacB

For the DNS assay, FTs containing 0.5 M sucrose solutions were incubated in 50 mm phosphate buffer pH 6.6 in a total volume of 500 µL at 650 rpm (Thermomixer compact, Eppendorf, Germany). Five samples of 70 µL each were taken at different time points after the reaction was started (0, 2, 4, 6 and 8) and mixed with 70 µL DNS. Samples were heated at 95° C. for 5 min and cooled down for 2 min at 4° C. For quantification, samples were diluted 1:6 with water and the absorbance measured at 540 nm. Data was processed using a calibration curve of absorbance versus glucose concentration and the change in absorbance (slope) was calculated.

Synthesis of D-glucuronic acid benzyl ester (5b)

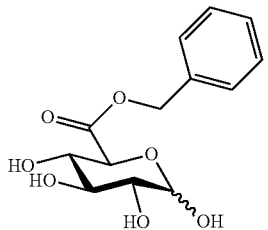

5b

D-glucuronic acid (4.00 g, 20.6 mmol) was dissolved in DMF (20 mL) and 1 M TBAF added (22 mL of 1 M solution in THF) at 0° C. Benzylbromide (3.52 g, 2.44 mL, 20.6 mmol) was dropped slowly to the reaction mixture at 0° C. and stirred at room temperature for a further 18 h. The solvent was removed under reduced pressure. The residue was purified via column chromatography over silica gel ($CH_2Cl_2$/MeOH 4:1) to yield ester 5b as colorless solid (4.21 g, 14.8 mmol, 72%). $R_f$: 0.50 ($CH_2Cl_2$/MeOH 4:1). $^1$H-NMR (400 MHz, $D_2O$/MeOD): δ=7.48-7.37 (m, 10 H, H—Ar, α/β), 5.28-5.25 (m, 4 H, H-7, α/ϵ), 5.24 (d, 1 H, $^3J$=3.9 Hz, H-1-α), 4.67 (d, 1 H, $^3J$=8.1 Hz, H-1β), 4.39 (d, 1 H, $^3J$=10.1 Hz, H-5-α), 4.11 (d, 1 H, $^3J$=9.8 Hz, H-5-β), 3.71 (dd, 1 H, $^3J$=9.4 Hz, $^3J$=9.4 Hz, H-3-α), 3.57 (dd, 1 H, $^3J$=10.1 Hz, $^3J$=9.4 Hz, H-4-α), 3.55 (dd, 1 H, $^3J$=9.4 Hz, $^3J$=3.9 Hz, H-2-α), 3.54 (dd, 1 H, $^3J$=9.8 Hz, $^3J$=9.2 Hz, H-4-β), 3.49 (dd, 1 H, $^3J$=9.2 Hz, $^3J$=9.2 Hz, H-3-β), 3.28 (dd, 1 H, $^3J$=8.1 Hz, $^3J$=9.2 Hz, H-2-β) ppm. $^{13}$C-NMR (101 MHz, $D_2O$/MeOD): δ=171.2 (COO-β), 170.3 (COO-α), 134.9 (2×Cq-Ar), 128.8 (3 C, 3×CH—Ar), 128.7 (2 C, 2×CH—Ar), 128.3 (4 C, 4×CH—Ar), 127.5 (CH—Ar), 96.2 (C-1-1-β), 92.4 (C-1-α), 75.2 (C-3-β), 74.7 (C-5-β), 73.6 (C-2-β), 72.3 (C-3-α), 71.5 (C-4-α), 71.3 (C-4-β), 70.9 (C-2-α), 70.7 (C-5-α), 67.9 (2 C, $OCH_2$, α/β) ppm. HRMS-ESI (+), m/z): 307.07882 [M+Na]$^+$, calcd. for $C_{13}H_{16}O_7Na^+$ 307.07866.

Synthesis of D-glucuronic acid iso-propylic ester (5c)

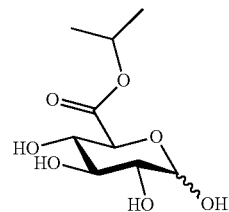

5c

D-glucuronic acid (4.00 g, 20.6 mmol) and $Ag_2CO_3$ (2.84 g, 10.3 mmol) were dissolved in 40 mL $H_2O$ and 40 mL MeOH and the mixture was stirred at room temperature for 1 h. The solvents were evaporated under reduced pressure and the resulting grey solid was dissolved in 100 mL DMF at 40° C. 2-Iodopropane (17.5 g, 10.3 mL, 103 mmol) was added and the reaction mixture was stirred for 4 h at 40° C. The resulting suspension was filtrated and the solvent of the filtrate was removed under reduced pressure. The residue was purified via column chromatography ($SiO_2$, $CH_2Cl_2$/MeOH 4:1) to achieve the ester 5c 2.39 g, 10.1 mmol, 49%) as a colorless solid. $R_f$: 0.32 ($CH_2Cl_2$/MeOH 4:1). $^1$H-NMR (400 MHz, $D_2O$/MeOD): δ=5.25 (d, 1 H, $^3J$=3.7 Hz, H-1-α), 5.14-5.04 (m, 2 H, H-7, α/β), 4.67 (d, 1 H, $^3J$=8.0 Hz, H-1β), 4.30 (d, 1 H, $^3J$=9.6 Hz, H-5-α), 3.98 (d, 1 H, $^3J$=9.6 Hz, H-5β), 3.71 (dd, 1 H, $^3J$=9.4 Hz, $^3J$=9.4 Hz, H-3-α), 3.56 (dd, 1 H, $^3J$=9.4 Hz, $^3J$=3.7 Hz, H-2-α), 3.55 (dd, 1 H, $^3J$=9.6 Hz, $^3J$=9.4 Hz, H-4-α), 3.52 (dd, 1 H, $^3J$=9.6 Hz, $^3J$=9.2 Hz, H-4β), 3.49 (dd, 1 H, $^3J$=9.2 Hz, $^3J$=9.2 Hz, H-3β), 3.28 (dd, 1 H, $^3J$=9.2 Hz, $^3J$=8.0 Hz, H-2β), 1.30-1.24 (m, 12 H, 4×$CH_3$, α/β) ppm. H-3-C-NMR (101 MHz, $D_2O$/MeOD): δ=171.0 (COO-β), 170.1 (COO-α), 96.2 (C-1-β), 92.4 (C-1-α), 75.2 (C-3-β), 74.8 (C-5-β), 73.6 (C-2β), 72.3 (C-3-α), 71.5 (C-4-β), 71.3 (2 C, C-7, α/β), 71.2 (C-4-α), 71.0 (C-2-α), 70.8 (C-5-α), 20.7 (4 C, 4×$CCH_3$, α/β) ppm.

Synthesis of β-D-fructofuranosyl-α-D-glucuronic acid benzyl ester (2b)

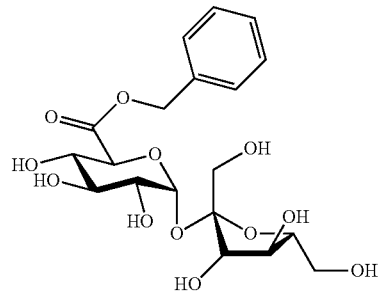

2b

To a solution of D-glucuronic benzyl ester (D-GlcABn) (3.64 g, 12.8 mmol) in Sorensen buffer pH 6.6 (128 µL, 1 M) and sucrose (2.19 g, 6.40 mmol in 2.56 mL $H_2O$ Bm-Ls (final activity 4 U/mL) was added and reacted at 37° C. for 1.5 h. The solvents were evaporated under reduced pressure. The residue was purified via column chromatography (silica-gel, EtOAc/iPrOH/$H_2O$ 6:3:1) to obtain the benzyl ester 2b as a colorless solid (1.29 g, 2.88 mmol, 45%). $R_f$: 0.45 (EtOAc/iPrOH/$H_2O$ 6:3:1). $^1$H-NMR (400 MHz, $D_2O$/MeOD): δ=7.48-7.37 (m, 5 H, H—Ar), 5.40 (d, 1H, $^3J$=3.9 Hz, H-1), 5.29 (m, 2 H, H-8), 4.40 (d, 1 H, $^3J$=9.9 Hz, H-5), 4.18 (d, 1 H, $^3J$=8.7 Hz, H-3'), 3.91 (dd, 1 H, $^3J$=8.7 Hz, $^3J$=8.7 Hz, H-4'), 3.80 (m, 1 H, H-5'), 3.75 (dd, 1 H, $^3J$=9.5 Hz, $^3J$=9.5 Hz, H-3), 3.62-3.57 (m, 4 H, H-2, H-4, 2×H-1'), 3.46 (m, 2 H, H-6') ppm. $^{13}$C-NMR (101 MHz, D$_2$O/MeOD): δ=170.7 (COO), 134.9 (1-C, Cq-Ar), 128.8 (3 C, CH—Ar), 126.5 (2 C, CH—Ar), 103.8 (C-2'), 92.2 (C-1), 81.5 (C-5'), 76.0 (C-3'), 73.8 (C-4'), 72.2 (C-3), 71.5 (C-5), 71.2 (C-4), 70.6 (C-2), 68.0 (C-7), 62.2 (C-6'), 60.9 (C-1') ppm. HRMS-ESI (+), m/z: 469.13165 [M+Na]$^+$ calcd. for C$_{19}$H$_{26}$O$_{12}$Na$^+$ 469.13099.

Synthesis of β-D-fructofuranosyl-α-D-glucuronic acid iso-propyl ester (2c)

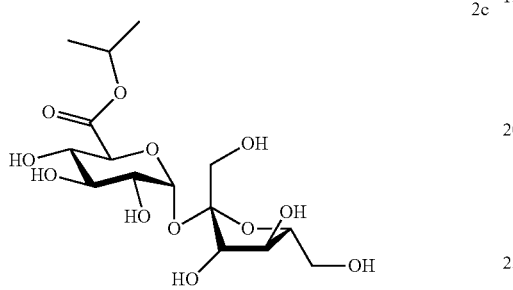

2c

To a solution of D-glucuronic iso-propyl ester (D-Glc-AiPr) (0.52 g, 2.20 mmol) in Sörensen buffer pH 6.6 (22 μL, 1 M) and sucrose (0.38 g, 1.10 mmol in 433 μL H$_2$O) Bm-Ls (final activity 4 U/mL) was added and reacted at 37° C. for 1.5 h. The solvents were evaporated under reduced pressure. The residue was purified via column chromatography (silica-gel, EtOAc/iPrOH/H$_2$O 6:3:1) to obtain the iso-propyl ester 2c as a colorless solid (0.32 g, 577 μmol, 52%). R$_f$: 0.40 (EtOAc/iPrOH/H$_2$O 6:3:1). $^1$H-NMR (400 MHz, D$_2$O/MeOD): δ=5.42 (d, 1 H, $^3J$=3.8 Hz, H-1), 5.12 (m, 1 H, H-7), 4.31 (d, 1 H, $^3J$=9.9 Hz, H-5), 4.21 (d, 1 H, $^3J$=8.7 Hz, H-3'), 3.99 (dd, 1 H, $^3J$=8.7 Hz, $^3J$=8.7 Hz, H-4'), 3.87 (ddd, 1 H, $^3J$=8.7 Hz, $^3J$=7.5 Hz, $^3J$=2.7 Hz, H-5'), 3.77-3.72 (m, 1 H, H-1'), 3.74 (dd, 1 H, $^3J$=9.9 Hz, $^3J$=9.3 Hz, H-3), 3.63 (m, 3 H, H-1', 2×H-6'), 3.59 (dd, 1 H, $^3J$=9.9 Hz, $^3J$=3.8 Hz, H-2), 3.56 (dd, 1 H, $^3J$=9.9 Hz, $^3J$=9.3 Hz, H-4), 1.30-1.27 (m, 6 H, 2×CH$_3$) ppm. $^{13}$C-NMR (101 MHz, D$_2$O/MeOD): δ=170.5 (COO), 103.9 (C-2'), 92.3 (C-1), 81.5 (C-5'), 76.0 (C-3'), 74.0 (C-4'), 72.3 (C-3), 71.7 (C-5), 71.4 (CCH$_3$), 71.2 (C-4), 70.5 (C-2), 62.3 (C-1'), 60.8 (C-6'), 20.5 (2 C, CCH$_3$) ppm. HRMS-ESI (+), m/z: 421.13165 [M+Na]$^+$ calcd. for C$_{15}$H$_{26}$O$_{12}$Na$^+$ 421.13160.

Synthesis of β-D-fructofuranosyl-α-D-glucuronic acid (2a)

2a

A mixture of β-D-fructofuranosyl-α-D-glucuronic iso-propyl ester (100 mg, 251 μmol) and 10 mL of a 0.5 M NaOH solution was stirred at room temperature for 1 h. DOWEX cation exchanger was added to the solution and stirred until pH 7 was reached. The solvents were evaporated under reduced pressure to obtain the sucrose acid 2a as a colorless solid (85.0 mg, 239 μmol, 95%). $^1$H-NMR (400 MHz, D$_2$O/MeOD): δ=5.40 (d, 1 H, $^3J$=3.9 Hz, H-1) 4.21 (d, 1 H, $^3J$=9.9 Hz, H-5), 4.19 (d, 1 H, $^3J$=8.7 Hz, H-3'), 4.03 (dd, 1 H, $^3J$=8.7 Hz, $^3J$=8.7 Hz, H-4'), 3.86 (ddd, 1 H, $^3J$=8.7 Hz, $^3J$=7.2 Hz, $^3J$=2.7 Hz, H-5'), 3.78-3.70 (m, 2 H, H-1', H-3), 3.68-3.56 (m, 4 H, H-1', 2×H-6', H-2), 3.51 (dd, 1 H, $^3J$=9.9 Hz, $^3J$=9.6 Hz, H-4) ppm. $^{13}$C-NMR (101 MHz, D$_2$O/MeOD): δ=174.5 (COO), 103.7 (C-2'), 92.1 (C-1), 81.4 (C-5'), 76.0 (C-3'), 73.7 (C-4'), 72.3 (C-3), 72.2 (C-5), 71.6 (C-4), 70.7 (C-2), 62.1 (C-6'), 60.8 (C-1') ppm.

Synthesis of D-galacturonic acid benzyl ester (6b)

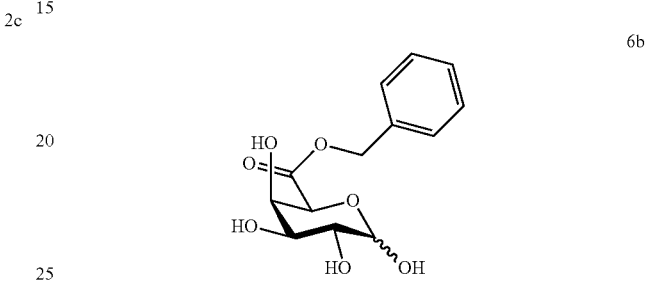

6b

D-galacturonic acid monohydrate (3.00 g, 14.1 mmol) was solved 48 mL DMF with molecular sieve 3 Å and 22 mL 1 M TBAF in THF was added at room temperature. Benzylbromide (2.41 g, 1.67 mL, 14.1 mmol) was added slowly at 0° C. and the reaction mixture was stirred for 72 h at room temperature. The solvent was removed under reduced pressure. The residue was purified via column chromatography over silica gel (CH$_2$Cl$_2$/MeOH 4:1) to yield ester 6b as colorless solid (2.52 g, 8.88 mmol, 63%). R$_f$: 0.47 (CH$_2$Cl$_2$/MeOH 4:1). $^1$H-NMR (400 MHz, D$_2$O/MeOD): δ=7.46-7.40 (m, 10 H, H—Ar α/β), 5.30 (d, 1 H, $^3J$=3.9 Hz, H-1-α) 5.27-5.24 (m, 4 H, OCH$_2$ α/β), 4.78 (m, 1 H, H-5-α), 4.58 (d, 1 H, $^3J$=7.9 Hz, H-1-β), 4.45 (d, 1 H, $^3J$=1.4 Hz, H-5-β), 4.31 (dd, 1 H, $^3J$=3.4 Hz, $^3J$=1.5 Hz, H-4-α), 4.24 (dd, 1 H, $^3J$=3.5 Hz, $^3J$=1.4 Hz, H-4-β), 3.89 (dd, 1 H, $^3J$=10.2 Hz, $^3J$=3.4 Hz, H-3-α), 3.79 (dd, 1 H, $^3J$=10.2 Hz, $^3J$=3.9 Hz, H-2-α), 3.67 (dd, 1 H, $^3J$=9.9 Hz, $^3J$=3.5 Hz, H-3-β), 3.49 (dd, 1 H, $^3J$=9.9 Hz, $^3J$=7.9 Hz, H-2-β) ppm. $^{13}$C-NMR (101 MHz, D$_2$O/MeOD): δ=170.7 (COO-β), 169.7 (COO-α), 135.0 (2 C, 2×Cq-Ar), 128.8 (4 C, 4×CH—Ar), 128.7 (2 C, 2×CH—Ar), 128.3 (4 C, 4×CH—Ar), 96.2 (C-1-β), 92.3 (C-1-α), 74.1 (C-3-β), 72.2 (C-5-β), 71.1 (C-2-β), 70.4 (C-3-α), 70.1 (C-4-α), 69.6 (C-4-β), 68.5 (C-2-α), 67.7 (C-5-α), 67.6 (2 C, OCH$_2$, α/β) ppm.

Synthesis of β-D-fructofuranosyl-α-D-galacturonic acid benzyl ester (3b)

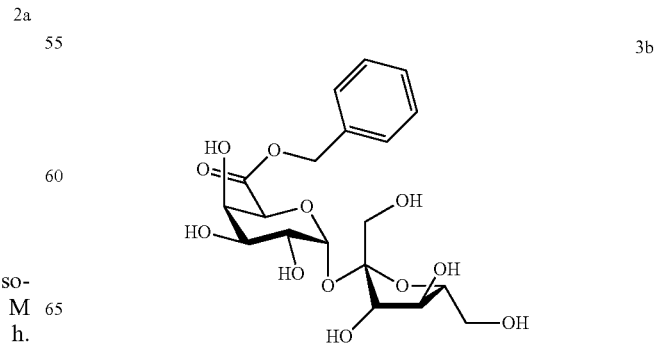

3b

To a solution of D-galacturonic benzyl ester (D-GalABn) (200 mg, 704 µmol) in Sorensen buffer (400 µL, 1 M) and sucrose (120 mg, 252 µmol in 8.00 mL H$_2$O) Bm-Ls (final activity 4 U/mL) was added and reacted at 37° C. for 1.5 h. The solvents were evaporated under reduced pressure. The residue was purified via column chromatography (silica-gel, CH$_2$Cl$_2$/MeOH 4:1) to obtain the benzyl ester 3b as a colorless solid (46.0 mg, 103 µmol, 41%). R$_f$: 0.26 (CH$_2$Cl$_2$/MeOH 4:1). $^1$H-NMR (400 MHz, D$_2$O/MeOD): δ=7.46-7.41 (m, 5 H, H—Ar), 5.46 (d, 1 H, $^3$J=3.9 Hz, H-1), 5.30-5.26 (m, 2 H, OCH$_2$), 4.85 (d, 1 H, $^3$J=1.5 Hz, H-5), 4.35 (dd, 1 Hz, H-4) 4.18 (d, 1 H, $^3$J=8.7 Hz, H-3'), 3.96 (dd, 1 H, $^3$J=10.2 Hz, $^3$J=3.4 Hz, H-3), 3.92 (dd, 1 H, $^3$J=8.7 Hz, $^3$J=8.7 Hz, H-4'), 3.86-3.81 (m, 2 H, H-2, H-5'), 3.64 (s, 2 H, 2×H-1'), 3.60-3.56 (m, 2 H, 2×H-6') ppm. $^{13}$C-NMR (101 MHz, D$_2$O/MeOD): δ=170.2 (COO), 135.1 (1-C, Cq-Ar), 128.8 (2 C, CH—Ar), 128.7 (1 C, CH—Ar) 128.4 (2 C, CH—Ar), 103.6 (C-2'), 92.3 (C-1), 81.3 (C-5'), 76.2 (C-3'), 73.7 (C-4'), 71.3 (C-3), 69.9 (C-5), 68.4 (C-4), 67.7 (C-2), 67.3 (C-7), 61.9 (C-6'), 60.9 (C-1') ppm.

Synthesis of β-D-fructofuranosyl-α-D-galacturonic acid (3a)

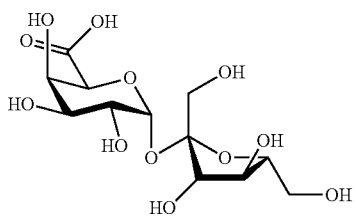

3a

A mixture of β-D-fructofuranosyl-α-D-galacturonic benzylic ester (46 mg, 103 µmol) and 5 mL of a 0.5 M NaOH solution was stirred at room temperature for 1 h. DOWEX anion exchanger was added to the solution 3 h at room temperature. The solvents were removed under reduced pressure to obtain the sucrose acid 3a as a colorless solid (35.3 mg, 99 µmol, 96%). $^1$H-NMR (400 MHz, D$_2$O/MeOD): δ=5.35 (d, 1 H, $^3$J=4.0 Hz, H-1), 4.46 (d, 1 H, $^3$J=1.5 Hz, H-5), 4.18 (dd, 1 H, $^3$J=3.4 Hz, $^3$J=1.5 Hz, H-4), 4.09 (d, 1 H, $^3$J=3.4 Hz, $^3$J=8.8 Hz, H-3'), 3.90 (dd, 1 H, $^3$J=8.8 Hz, $^3$J=8.8 Hz, H-4'), 3.88 (dd, 1 H, $^3$J=10.4 Hz, $^3$J=3.4 Hz, H-3), 3.78-3.71 (m, 2 H, H-2, H-6'), 3.65 (dd, 1 H, $^2$J=12.6 Hz, $^3$J=2.9 Hz, H-6'), 3.61-3.55 (m, 3 H, H-5', 2×H-1') ppm. $^{13}$C-NMR (101 MHz, D$_2$O/MeOD): δ=174.2 (COO), 103.6 (C-2'), 92.4 (C-1), 81.3 (C-5'), 76.3 (C-3'), 73.7 (2 C, C-4', C-3), 70.4 (C-5), 68.9 (C-4), 67.5 (C-2), 61.8 (C-6'), 60.8 (C-1') ppm.

6-O-Toluolsulfonyl-D-glucopyranose (400 MHz, D$_2$O/MeOD): δ=7.81-7.77 (m, 4 H, H$_{arom}$-Ts), 7.44-7.42 (m, 4 H, H$_{arom}$-Ts), 5.00 (d, J=3.68 Hz, 1 H, H1α), 4.42 (d, J=7.80 Hz, 1 H, H1β), 4.28 (m, 2 H, H6α, H6β), 4.16 (m, 2 H, H6α, H6β), 4.16 (dd, J=5.42, 10.58 Hz, 1 H, H6α), 4.11 (dd, J=6.16, 10.56 Hz, 1 H, H6β), 3.90 (ddd, J=2.03, 5.37, 10.05 Hz, 1 H, H5α), 3.61 (t, J=9.28 Hz, 1 H, H3α), 3.43 (ddd, J=1.97, 6.19, 9.73 Hz, 1 H, H5β), 3.28-3.25 (m, J=15.97 Hz, 2 H, H3α, H2β), 3.22-3.17 (m, 2 H), 3.08 (dd, J=7.84, 9.16 Hz, 1 H, H2β), 2.45 (s, 1 H, H-Me an Ts) ppm. $^{13}$C-NMR (101 MHz, D$_2$O/MeOD): δ=149.99 (1 C, Carom-Ts), 146.51 (2 C, Carom-Ts), 138.76 (1 C, Carom-Ts), 134.47 (2 C, Carom-Ts), 131.05 (2 C, Carom-Ts), 129.94 (1 C, Carom-Ts), 129.20 (1 C, Carom-Ts), 127.07 (1 C, Carom-Ts), 125.75 (1 C, Carom-Ts), 98.28 (1 C, 1β), 94.02 (1 C, C1α), 77.99 (1 C, C2α), 76.13 (1 C, C2α), 75.20 (1 C, C5α), 74.81 (1 C, C3α), 73.68 (1 C, C3β), 71.52 (2 C, C6α, C6β), 71.35 (2 C, C4α, C4β), 71.18 (1 C, 5α), 21.65 (2 C, C-Me an Ts) ppm.

Synthesis of 6-O-Toluolsulfonyl-D-glucopyranosyl-β-D-fructofuranoside

6-O-Toluolsulfonyl-D-glucopyranose (100 mg, 0.23 mmol) and sucrose (6.14 g, 4.80 mmol) are solved in 1 M Sorensen-buffer (5 mL, pH 6.6). The enzyme is added (SacB, 2U). The reaction mixture can be stirred for 1 h at 37° C. The reaction will be stopped by adding 5 mL methanol. The product will be isolated over silica gel with an eluent (water/isopropanol/acidic acid ethylester=1:3:6). 1H-NMR (400 MHz, MeOD):

δ=7.81 (d, J=1.24, 7.15 Hz, 2 H, Harom-Ts), 7.45 (J=8.80 Hz, 2 H, Harom-Ts), 5.28 (d, J=3.76 Hz, 1 H, H1), 4.28 (dd, J=1.91, 10.64 Hz, 1 H, H6), 4.14 (dd, J=10.75, 5.17 Hz, 1 H, H6), 4.06 (d, J=8.26 Hz, 1 H, H3'), 3.98 (ddd, J=1.88, 5.07, 10.14 Hz, 1 H, H5), 3.91 (t, J=8.06 Hz, 1 H, H4'), 3.80-3.66 (m, 4 H, 5 H, H5', H6', H3), 3.56 (m, J=8.8 Hz, 2 H, H1', H2'), 3.33 (m, 1 H, H2), 3.22 (dd, J=8.93, 10.28 Hz, 1 H, H4), 2.46 (s,3 H, H-Me an Ts) ppm.

13C NMR (100-MHz, MeOD):

δ=146.62 (1 C, Carom-Ts), 134.30 (1 C, Carom-Ts), 131.13 (2 C, Carom-Ts), 129.30 (2 C, Carom-Ts), 105.28 (1 C, C2'), 93.40 (1 C, C1), 84.14 (1 C, C5'), 79.29 (1 C, C3'), 76.05 (1 C, C4'), 74.60 (1 C, C3), 73.10 (1 C, C2), 71.90 (1 C, C5), 71.19 (1 C, C4), 70.83 (1 C, C6), 64.28-64.16 (2 C, C1', C6'), 21.69 (1 C, C-Me an Ts) ppm.

Synthesis of 6-Azido-6-desoxy-D-glucopyranosyl-β-D-fructofuranoside 17.5 mg (35.2 µmol) of 6-O-Toluolsulfonyl-D-glucopyranosyl-β-D-fructofuranoside are solved in DMF (2 mL) and 9.02 mg (0.139 mmol) sodium azide added. The mixture is stirred 96 h at 120° C. Isolation of the product can be done with silica gel and an eluent (water/isopropanol/acidic acid ethylester=1:3:6) and 0.5% triethylamine. 1H-NMR (400 MHz, MeOD): δ=5.40 (d, J=3.96 Hz, 1 H, H1), 4.10 (d, J=8.33 Hz, 1 H, H3'), 4.01 (t, J=8.09 Hz, 1 H, H4'), 3.96 (ddd, J=2.47, 4.75, 9.89 Hz, 1 H, H5), 3.81-3.75 (m, 3 H, H5', H6'), 3.69 (t, J=9.47 Hz, 1 H, H3), 3.45-3.40 (m, 2 H, H2, H6) 3.34 (s, 1 H, H4) ppm.13C-NMR (100 MHz, MeOD):

δ=105.44 (1 C, C2'), 93.67 (1 C, C1), 83.99 (1 C, C5'), 79.26 (1 C, C3'), 75.96 (1 C, C4'), 74.56 (1 C, C3), 73.32 (1 C, C4), 73.20 (1 C, C2), 72.16 (1 C, C5), 64.09-63.89 (2 C, C1, C6'), 52.78 (1 C, C6) ppm.

The invention claimed is:

1. A method for the preparation of a β-D-fructofuranosyl-(2,1)-α-D-uronic acid or an ester thereof which comprises the step of fructosylating a D-uronic acid salt or ester thereof in the presence of *B. megaterium* levansucrase (Bm-Ls).

2. The method of claim 1, wherein the D-uronic acid is D-galacturonic acid or D-glucuronic acid.

3. The method of claim 1, wherein the D-uronic acid salt is an alkali metal salt.

4. The method of claim 1, wherein the ester is a residue of the formula—CO—O—R, wherein R is a hydrocarbon residue having 1 to 30 carbon atoms which may be interrupted by one or more heteroatoms and which may be substituted by one or more functional groups.

5. The method of claim 1, wherein the method is for the preparation of a β-D-fructofuranosyl-(2,1)-α-D-uronic acid ester, further wherein an esterification step is conducted prior or after the fructosylation step.

6. The method of claim 5, wherein the esterification step is conducted in the presence of tetrabutylammonium fluoride.

7. The method of claim 3, wherein the alkali metal salt is sodium salt.

* * * * *

UNITED STATES PATENT AND TRADEMARK OFFICE
CERTIFICATE OF CORRECTION

| | |
|---|---|
| PATENT NO. | : 11,377,463 B2 |
| APPLICATION NO. | : 16/645380 |
| DATED | : July 5, 2022 |
| INVENTOR(S) | : Christian Possiel et al. |

It is certified that error appears in the above-identified patent and that said Letters Patent is hereby corrected as shown below:

In the Specification

At Column 3, Line 67, replace "8" with -- β --.

At Column 4, Line 65, replace "8" with -- β --.

At Column 5, Line 2, replace "8" with -- β --.

At Column 5, Line 29, replace "8" with -- β --.

At Column 6, Line 31, replace "3" with -- β --.

At Column 9, Line 52, replace "ϵ" with -- β --.

At Column 10, Line 29, replace "13" with -- β --.

At Column 12, Line 4, replace "5" with -- δ --.

At Column 13, Line 46, replace "5" with -- δ --.

At Column 13, Line 63, replace "α" with -- β --.

Signed and Sealed this
Fifteenth Day of August, 2023

*Katherine Kelly Vidal*

Katherine Kelly Vidal
*Director of the United States Patent and Trademark Office*